US010947499B2

(12) United States Patent
Preynat-Seauve et al.

(10) Patent No.: US 10,947,499 B2
(45) Date of Patent: Mar. 16, 2021

(54) SELECTION OF STEM CELL CLONES WITH DEFINED DIFFERENTIATION CAPABILITIES

(75) Inventors: Olivier Preynat-Seauve, Habare-Lullin (FR); Karl-Heinz Krause, Geneva (CH)

(73) Assignee: Research Development Foundation, Carson City, NV (US)

( * ) Notice: Subject to any disclaimer, the term of this patent is extended or adjusted under 35 U.S.C. 154(b) by 805 days.

(21) Appl. No.: 12/958,183

(22) Filed: Dec. 1, 2010

(65) Prior Publication Data

US 2011/0136681 A1 Jun. 9, 2011

Related U.S. Application Data

(60) Provisional application No. 61/266,072, filed on Dec. 2, 2009.

(51) Int. Cl.
| | |
|---|---|
| *C12N 5/0735* | (2010.01) |
| *G01N 33/50* | (2006.01) |
| *A61P 3/10* | (2006.01) |
| *A61P 9/10* | (2006.01) |

(52) U.S. Cl.
CPC ....... *C12N 5/0606* (2013.01); *G01N 33/5014* (2013.01); *G01N 33/5044* (2013.01); *A61P 3/10* (2018.01); *A61P 9/10* (2018.01); *C12N 2503/02* (2013.01)

(58) Field of Classification Search
CPC .............. G01N 33/5044; C12N 5/0606; A61K 48/0075; A61K 31/7052
See application file for complete search history.

(56) References Cited

U.S. PATENT DOCUMENTS

| | | | | |
|---|---|---|---|---|
| 5,843,780 | A | 12/1998 | Thomson | 435/363 |
| 6,200,806 | B1 | 3/2001 | Thomson | 435/366 |
| 6,325,114 | B1 | 12/2001 | Bevirt et al. | 141/130 |
| 6,833,269 | B2 | 12/2004 | Carpenter | 435/377 |
| 7,029,913 | B2 | 4/2006 | Thomson | 435/363 |
| 2003/0017589 | A1 | 1/2003 | Mandalam et al. | 435/366 |
| 2005/0153445 | A1 | 7/2005 | Mandalam et al. | 435/366 |
| 2005/0255592 | A1 | 11/2005 | Collins et al. | |
| 2006/0063253 | A1 | 3/2006 | Maciag et al. | 435/325 |
| 2006/0252150 | A1 | 11/2006 | Cheng | 435/372 |
| 2006/0263879 | A1* | 11/2006 | Simon Valles | C12N 5/0606 435/366 |
| 2007/0253937 | A1 | 11/2007 | Yoon et al. | |
| 2008/0171385 | A1 | 7/2008 | Bergendahl et al. | 435/384 |
| 2008/0254004 | A1* | 10/2008 | Terskikh | C12N 5/0623 424/93.7 |

FOREIGN PATENT DOCUMENTS

| | | |
|---|---|---|
| CN | 101126080 | 2/2008 |
| WO | WO 2009-143241 | 11/2009 |

OTHER PUBLICATIONS

Gerrard et al (Stably Transfected Human Embryonic Stem Cell Clones Express OCT4-Specific Green Fluorescent Protein and Maintain Self-Renewal and Pluripotency, Stem Cells, 23: 124-133, 2006).*
Martinez et al (J. Cell. Mol. Med, 16, No. 3: pp. 456-467, 2012).*
Morizane et al (Journal of Neuroscience Research 83:1015-1027 (2006)).*
Xu et al (Circ Res, 91: 501-508, 2002).*
Yu et al (Science 324 (5928): 797-801, 2009, published on line Mar. 26, 2009).*
Amit et al (Developmental Biology, 227: 271-278, 2000).*
Cai et al (Hepatology, 45: 1229-1239, 2007).*
Heins et al (Journal of Biotechnology, 122: 511-520, 2006); (Year: 2006).*
Stewart et al, (Nature Methods, 3(10): 807-815, 2006). (Year: 2006).*
Cho et al., "Highly efficient and large-scale generation of functional dopamine neurons from human embryonic stem cells," *PNAS*, 105(9):3392-3397, 2008.
Office Action issued in Japanese Application No. 2012-542160, dated Nov. 5, 2014, and English language translation thereof.
PCT International Search Report and Written Opinion issued in International Application No. PCT/US2010/058570, dated Aug. 12, 2011.
Agalliu and Schieren, "Heterogeneity in the developmental potential of motor neuron progenitors revealed by clonal analysis of single cells in vitro," *Neural Development*, 4:2, doi: 10.11861/1749-8104-4-2, 2009.
Amit et al., "Clonally derived human embryonic stem cell lines maintain pluripotency and proliferative potential for prolonged periods of culture," *Dev. Bio.*, 227:271-278, 2000.
Bean et al., "Coherence and timing of cell cycle start examined at single-cell resolution," *Mol. Cell.*, 21:3-14, 2006.

(Continued)

*Primary Examiner* — Anoop K Singh
*Assistant Examiner* — Magdalene K Sgagias
(74) *Attorney, Agent, or Firm* — Parker Highlander PLLC

(57) ABSTRACT

Disclosed are methods for producing a clonal population of cells involving: a) obtaining a population of pluripotent or multipotent cells that have been expanded in vitro and maintained in an undifferentiated or essentially undifferentiated state; b) expanding individualized cells of the population into clonal populations of cells; and c) selecting one or more clonal population of cells determined to have the ability to differentiate into a population that is at least about 50% homogeneous for either neural cell types, hepatocytes, or cardiomyocytes. Also disclosed are clonal populations of cells produced by the methods of the present invention, and methods of treating disease in subjects involving administration of clonal cells of the present invention to a subject. Methods of screening test compounds that involve contacting a test compound with a clonal population of cells produced by the methods of the present invention are also set forth.

25 Claims, 10 Drawing Sheets

(56) References Cited

OTHER PUBLICATIONS

Canham et al., "Functional heterogeneity of embryonic stem cells revealted through translational amplification of an early endodermal transcript," *PLoS Biol.*, 8:e1000379, May 2010.
Chambers et al., "Highly efficient neural conversion of human ES and iPS cells by dual inhibition of SMAD signaling," *Nat. Biotechnol.*, 27:275-280, 2009.
Chazaud et al., "Early lineage segregation between epiblast and primitive endoderm in mouse blastocysts through the Grb2-MAPK pathway," *Dev. Cell*, 10:615-624, 2006.
Chen et al., "Single cell derived murine embryonic stem cells clones stably express Rexl-specific green fluorescent protein and their differentiation study," *Biochem. Biophys. Res. Commun.*, 362(2):467-73, 2007.
Chuykin et al., "Characterization of trophoblast and extraembryonic endoderm cell lineages derived from rat preimplantation embryos," *PLoS One*, 5(3):e9794, Mar. 2010.
Gardner et al., "Investigation of cell lineage and differentiation in the extraembryonic endoderm of the mouse embryo," *J. Embryol. Exp. Morphol.*, 68:175-198, 1982.
Goetz et al., "United Parkinson Foundation Neurotransplantation Registry on adrenal medullary transplants: presurgical, and 1- and 2-year follow-up," *Neurology*, 41:1719-1722, 1991.
Hasegawa et al., "A method for the selection of human embryonic stem cell sublines with high replating efficiency after single-cell dissociation," *Stem Cells*, 24:2649-2660, 2006.
Hayashi et al., "Dynamic equilibrium and heterogeneity of mouse pluripotent stem cells with distinct functional and epigenetic states," *Cell Stem Cell*, 3:391-401, 2008.
Hentze et al., "Teratoma formation by human embryonic stem cells: Evaluation of essential parameters for future safety studies," *Stem Cell Res.*, vol. 2, Issue 3, May 2009, pp. 198-210 Epub ahead of print, Feb. 12, 2009.
Kollmann et al., "Design principles of a bacterial signaling network," *Nature*, 438:504-507, 2005.
Li et al., "The NADPH oxidase NOX4 drives cardiac differentiation: Role in regulating cardiac transcription factors and MAP kinase activation," *Mol. Biol. Cell.*, 17:3978-3988, 2006.
Lyons et al., "Analysing cell division in vivo and in vitro using flow cytometric measurement of CFSE dye dilution," *J. Immunol. Methods*, 243(1-2):147-54, 2000.
Mareddy et al., "Stem cell related gene expression in clonal populations of mesenchymal stromal cells from bone marros," *Tissue Engineering*, Part A, 16(2):749-758, 2010.
Mchedlishvili et al., "A clonal analysis of neural progenitors during axolotl spinal cord regeneration reveals evidence for both spatially restricted and multipotent progenitors," *Development*, 134:2083-2093, 2007.
Meilhac et al., "Active cell movements coupled to positional induction are involved in lineage segregation in the mouse blastocyst," *Dev. Biol.*, 331:210-221, 2009.
Morris et al., "Origin and formation of the first two distinct cell types of the inner cell mass in the mouse embryo," *Proc. Natl. Acad. Sci. USA*, 107:6364-6369, 2010.
Nicholas et al., "A method for single-cell sorting and expansion of genetically modified human embryonic stem cells," *Stem Cells Dev.*, 16(1):109-17, 2007.
Noctor et al., "Neural stem and progenitor cells in cortical development," *Novartis Found. Symp.*, 288:59-73, discussion 73-78 and general discussion 1 96-98, 2007.
Ono et al., "Muscle satellite cells are a functionally heterogeneous population in both somite-derived and branchiomeric muscles," *Developmental Biology*, 337(1):29-41, 2010.
Peng and Chen, "[Establishment and characteristics of clonal human embryonic stem cell lines]," *Zhonghua Fu Chan Ke Za Zhi*, 40(8):521-4, 2005. Abstract (English summary; article in Chinese).
Pick et al., "Clone and gene specific aberrations of parental imprinting in human induced pluripotent stem cells," *Stem Cells*, 27:2686-2690, 2009.
Plusa et al., "Distinct sequential cell behaviors direct primitive endoderm formation in the mouse blastocyst," *Development*, 135:3081-3091, 2008.
Raj, "Medical evaluation of panic attacks," *J. Clin. Psychiatry*, 48:309-313, 1987.
Ravin et al., "Potency and fate specification in CNS stem cell populations in vitro," *Cell Stem Cell*, 3:670-680, 2008.
Reubinoff et al., "Embryonic stem cell lines from human blastocysts: somatic differentiation in vitro," *Nat. Biotechnol.*, 18:399-404, 2000.
Rietz and Reynolds, "Neural stem cell isolation and characterization," *Methods Enzymol*, 419:3-23, 2006.
Rossant et al., "Lineage allocation and asymmetries in the early mouse embryo," *Philos. Trans. R. Soc. Lond. B. Biol. Sci*, 358:1341-1348, 2003; discussion on p. 1349.
Schmandt et al., "High-purity lineage selection of embryonic stem cell-derived neurons," *Stem Cells Dev.*, 14:55-64, 2005.
Shahrezaei and Swain, "The stochastic nature of biochemical networks," *Curr. Opin. Biotechnol.*, 19:369-374, 2008.
Shintani et al., "Generation of dopamine neurons from embryonic stem cells in the presence of the neutralizing activity of bone marrow stromal cells derived from adult mice," *J. Neurosci. Res.*, 86:2829-2838, 2008.
Sidhu and Tuch, "Derivation of three clones from human embryonic stem cell lines by FACS sorting and their characterization," *Stem Cells Dev.*, 15(1):61-9, 2006.
Sigal et al., "Variability and memory of protein levels in human cells," *Nature*, 444:643-646, 2006.
Singh et al., "A heterogeneous expression pattern for Nanog in embryonic stem cells," *Stem Cells*, 25:2534-2542, 2007.
Smith, "Embryo-derived stem cells: of mice and men," *Annu. Rev. Cell. Dev. Biol.*, 17:435-462, 2000.
Srivastava et al., "Potentials of ES cell therapy in neurodegenerative diseases," *Curr. Pharm. Des.*, 14:3873-3879, 2008.
Stewart et al., "Clonal isolation of hESCs reveals heterogeneity within the pluripotent stem cell compartment," *Nat. Methods*, 3(10):807-15, 2006.
Suter et al., "Phenazopyridine induces and synchronizes neuronal differentiation of embryonic stem cells," *J. Cell. Mol. Med.*, 13(9B):3517-27, 2009.
Svendsen et al., "Human neural stem cells: isolation, expansion and transplantation," *Brain Pathol.*, 9(3):499-513, 1999.
Takahashi and Yamanaka, "Induction of pluripotent stem cells from mouse embryonic and adult fibroblast cultures by defined factors," *Cell*, 126:663-676, 2006.
Takahashi et al., "Induction of pluripotent stem cells from adult human fibroblasts by defined factors," *Cell*, 131:861-872, 2007.
Tesar et al., "New cell lines from mouse epiblast share defining features with human embryonic stem cells," *Nature*, 448:196-199, 2007.
Thomson and Marshall, "Primate embryonic stem cells," *Curr. Top. Dev. Biol.*, 38:133-165, 1998.
Thomson and Odorico, "Human embryonic stem cell and embryonic germ cell lines," *J. Trends. Biotechnol.*, 18:53-57, 2000.
Thomson et al., "Embryonic stem cell lines derived from human blastocysts," *Science*, 282:1145-47, 1998.
Thomson et al., "Isolation of a primate embryonic stem cell line," *Proc. Natl. Acad. Sci. USA*, 92:7844-7848, 1995.
Toyooka et al., "Identification and characterization of subpopulations in undifferentiated ES cell culture," *Development*, 135:909-918, 2008.
Watanabe et al., "A ROCK inhibitor permits survival of dissociated human embryonic stem cells," *Nature Biotechnology*, 25(6):681-6, 2007.
Weinberger et al., "Stochastic gene expression in a lentiviral positive-feedback loop: HIV-1 Tat fluctuations drive phenotypic diversity," *Cell*, 122:169-182, 2005.
Xu et al., "Feeder-free growth of undifferentiated human embryonic stem cells," *Nat. Biotechnol.*, 19:971-974, 2001.
Ying et al., "BMP induction of Id proteins suppresses differentiation and sustains embryonic stem cell self-renewal in collaboration with STAT3," *Cell*, 115:281-292, 2003.

(56) References Cited

OTHER PUBLICATIONS

Yu and Thomson, "Pluripotent stem cell lines," *Genes Dev.*, 22(15):1987-97, 2008.
Yu et al., "Induced pluripotent stem cell lines derived from human somatic cells," *Science*, 318:1917-1920, 2007.
Office Action issued in Chinese Application No. 201080062827.5, dated Dec. 10, 2013.
Canham et al., "Functional heterogeneity of murine embryonic stem cells revealed through translational amplification in an early endoderm marker," *Mechanisms of Development*, 126:S280-S281, Abstract 17-P035, 2009.
Extended European Search Report issued in European Application No. 10835060.4, dated Sep. 26, 2013.
Office Action issued in Australian Application No. 2010326106, dated Nov. 25, 2013.
Office Action issued in Australian Application No. 2010326106, dated Dec. 19, 2014.
Office Action issued in Chinese Application No. 201080062827.5, dated Mar. 25, 2013, and English language translation thereof.
Office Action issued in European Application No. 10835060.4, dated May 14, 2014.

\* cited by examiner

SELECTION OF STEM CELL CLONES WITH DEFINED DIFFERENTIATION CAPABILITIES

This application claims priority to U.S. Application No. 61/266,072 filed on Dec. 2, 2009, the entire disclosure of which is specifically incorporated herein by reference in its entirety without disclaimer.

BACKGROUND OF THE INVENTION

1. Field of the Invention

The present invention relates generally to the fields of stem cell selection, stem cell differentiation, and cell therapy. More particularly, it concerns methods for the selection of non-genetically modified clonal pluripotent stem cell lines. with defined differentiation abilities, and applications of the stem cell clones produced by the methods of the present invention.

2. Description of Related Art

Pluripotent stems cells, including embryonic stem (ES) cells and induced pluripotent stem cells, hold great promise for studying early development, modelizing disease and toxicology, as well as for use in cell therapy. The same is true of adult and embryonic neural stem cells. Because such cells can proliferate in culture and maintain their potential for differentiating into different cell types, they can provide an almost unlimited supply of cells for treating a variety of diseases.

One active area of research is the treatment of nervous system diseases and cardiovascular diseases using cell therapy. An approach to the treatment of degenerative nervous system diseases is to transplant cells of the central nervous system, such as dopaminergic neurons, into affected areas of the nervous system.

Potential sources of cells for cell therapy are prepared by differentiating ES cells, induced pluripotent stem (iPS) cells and other types of stem cells in vitro. Methods of preparing primate ES cell cultures have been described for human, rhesus monkey, and marmoset ES cells (U.S. Pat. Nos. 5,843,780; 6,200,806; 7,029,913).

Unfortunately, although a heterogeneous mixture of different cell types derived from pluripotent stem cells is easy to obtain in culture, their targeted differentiation towards a specific lineage remains challenging. In general, differentiation of ES cells in culture produces a heterogeneous mixture of cells, only some of which may be differentiated cells suitable for cell therapy, such as neural cells.

A more controlled differentiation process would strongly help to the improvement of neural cell and tissue engineering from stem cells. Thus, there is the need for improved methods of preparing differentiated cells from stem cells for use in cell therapy.

SUMMARY OF THE INVENTION

The present invention is based in part on the identification of methods for providing a clonal population of pluripotent stem cells with a specific or particular differentiation potential. The methods of the present invention have the benefit of providing for enriched populations of differentiated cells that can be applied in cell therapies or biotechnologies that utilize ESC. In addition, use of purified or highly purified differentiated cells in therapeutic applications reduces the risk of adverse effects in a subject, such as the risk of teratoma or neuroepithelial tumors following transplantation of cells into the brain. Further, the methods of the present invention may provide for a clonal population of cells that are not genetically modified.

Included in the present invention are methods for producing or generating a clonal population of cells, involving a) obtaining a population of pluripotent or multipotent cells that have been expanded in vitro and maintained in an undifferentiated or essentially undifferentiated state; b) expanding individualized cells of the population into clonal populations of cells; and c) selecting one or more clonal population of cells determined to have the ability to differentiate into a population that is at least about 50% homogeneous for either neural cell types, hepatocytes, muscle cells or cardiomyocytes. In certain embodiments, the method may further involve providing cells, or their progeny, of the one or more selected population of cells. As shown in the below examples, increases in hepatocyte-typical markers in certain clonal pluripotent cell lines was increased about 100 fold during differentiation towards embryoid bodies.

A "clonal population of cells" is defined herein to refer to a group of cells that are descended from a single common ancestor cell.

The term "pluripotent stem cell" refers to a cell capable of giving rise to cells of all three germinal layers, that is, endoderm, mesoderm and ectoderm. Although in theory a pluripotent cell can differentiate into any cell of the body, the experimental determination of pluripotency is typically based on differentiation of a pluripotent cell into several cell types of each germinal layer. In some embodiments of the present invention, a pluripotent stem cell is an embryonic stem (ES) cell derived from the inner cell mass of a blastocyst. In other embodiments, the pluripotent stem cell is an induced pluripotent stem cell derived by reprogramming differentiated cells. In certain embodiments, the pluripotent stem cell is an embryonic stem cell derived by somatic cell nuclear transfer. The pluripotent cells may be a human embryonic stem cells. Non-limiting examples of human embryonic stem cells include H1, H9, hES2, hES3, hES4, hES5, hES6, BG01, BG02, BG03, HSF1, HSF6, H1, H7, H9, H13B, and H14. The pluripotent cells may be induced pluripotent cells (iPSC), as discussed in greater detail below. Non-limiting examples of iPSC include iPS 6.1, iPS 6.6, iPS, iPS 5.6, iPS 5.12, iPS 5.2.15, iPS 5.2.24, iPS 5.2.20, iPS 6.2.1, and iPS 5/3-4.3. The method may further comprise expanding the selected clonal population of cells. The method may further comprise determining whether cells have the ability to differentiate into a population that is at least about 50% homogeneous for either neural cells, hepatocytes, or cardiomyocytes. The method may further comprise providing the selected clonal population of cells. The method may further comprise preparing the selected clonal population of cells for storage or shipment. Said preparing the cells for storage or shipment may comprise freezing the cells.

The term "multipotent stem cell" refers to a stem cell that is capable of differentiating into a limited number of tissue types. Non-limiting examples of multipotent stem cells include neural stem cells and hematopoietic stem cells. A "neural stem cell" is an undifferentiated cell from neural tissue that is capable of giving rise to more neural stem cells (i.e., exhibits self renewal) and to progeny cells that will terminally differentiate into neural cells. The neural stem cell can be an adult or embryonic neural stem cell.

The term "cardiomyocyte" as used herein refers to (a) a cell that exhibits one or more morphological features that are known to be present in mature or immature cardiomyocytes; or (b) a cell that expresses one or more markers or other proteins that are known to be present in mature or immature cardiomyocytes. Thus, the term "cardiomyocyte" as used herein refers to both mature or immature cardiomyocytes. Non-limiting examples of morphological features include formation of beating muscle cells, expression of cardiac-specific sarcomeric proteins, and expression of ion channels. Non-limiting examples of markers include cardiac troponin I (cTnI), cardiac troponin T (cTnT), sarcomeric myosin heavy chain (MHC), GATA-4, Nkx2.5, N-cadherin, beta.1-adrenoceptor (β1-AR), ANF, the MEF-2 family of transcription factors, creatine kinase MB (CK-MB), myoglobin, and atrial natriuretic factor (Li et al., 2006).

A "neural cell" as used herein refers to (a) a cell that exhibits one or more morphological features that are known to be present in mature neurons, immature neurons, mature glial cells, immature glial cells, or neural progenitor cells; or (b) a cell that expresses one or more markers, neurotransmitters, or other proteins that are known to be present in mature neurons, immature neurons, mature glial cells, immature glial cells, or neural progenitor cells. Non-limiting examples of morphological features include small cell bodies, multiple processes reminiscent of axons, and dendrites. Non-limiting examples of markers, neurotransmitters, or other proteins include: a) β3-tubulin, microtubule-associated protein 2 (MAP-2), or neurofilament, characteristic of neurons; b) glial fibrillary acidic protein (GFAP), present in astrocytes; c) 2', 3'-cyclic nucleotide 3'-phosphodiesterase (CNPase) galactocerebroside (GalC) or myelin basic protein (MBP), characteristic of oligodendrocytes; d) Oct-4, characteristic of undifferentiated ES cells; e) Pax-6 and nestin, characteristic of neural precursors and other cells; f) Sox 1, characteristic of developing central nervous system; g) tyrosine hydroxylase (TH), present in catecholamine neurons; h) glutamic acid decarboxylase, isoform 67 (GAD67), present in neurons containing gamma-aminobutyric acid; i) vimentin, characteristic of intermediate neural differentiation; and j) dopamine secretion, radioactive dopamine uptake and dopamine transporter expression, which are signatures for dopaminergic differentiation. Non-limiting examples of "glial cells" include astrocytes, oligodendrocytes, ependymal cells, radial glia, Schwann cells, and satellite cells. A "neural cell" as used herein includes a "neuronal cell." A "neuronal cell" as used herein refers to a mature or immature neuron. For example, the mature or immature neuron may be a mature or immature dopaminergic neuron.

The term "hepatocyte" as used herein refers to (a) a cell that exhibits one or more morphological features that are known to be present in mature or immature hepatocyte; or (b) a cell that expresses one or more markers or other proteins that are known to be present in mature or immature hepatocytes. Thus, the term "hepatocyte" as used herein refers to both mature or immature hepatocytes. Non-limiting examples of morphological features includes eosinophilic cytoplasm, numerous mitochondria and basophilic stippling, round nuclei with dispersed chromatin and prominent nucleoli. Hepatocytes may also be identified by identification of expression of liver-specific proteins including alpha-foeto protein, albumin. Additional methods that may be used to distinguish hepatocytes includes electron microscopy, immunocytochemistry, immunofluorescence, quantitative PCR, western blotting, and in situ hybridization.

The selected clonal population of cells may exhibit a cardiogenic differentiation potential. The selected clonal population of cells may exhibit a hepatocyte differentiation potential. Alternatively, the clonal population of cells may exhibit a neurogenic differentiation potential. The clonal population of cells that exhibit a neurogenic differentiation potential may exhibit differentiation into any particular type of neural cell. Non-limiting examples include neurons, oligodendrocytes, astrocytes, microglial cells, satellite cells, and Schwann cells. In particular embodiments, the neural cells are dopaminergic neurons.

In some embodiments, the selected clonal population of cells may show the ability to differentiate into at least 55% neural cells, at least 60% neural cells, at least 65% neural cells, at least 70% neural cells, at least 75% neural cells, at least 80% neural cells, at least 85% neural cells, at least 90% neural cells, at least 95% neural cells, or at least 99% neural cells, or any range derivable therein. In other embodiments, the selected clonal population of cells may show the ability to differentiate into at least 55% cardiomyocytes, at least 60% cardiomyocytes, at least 65% cardiomyocytes, at least 70% cardiomyocytes, at least 75% cardiomyocytes, at least 80% cardiomyocytes, at least 85% cardiomyocytes, at least 90% cardiomyocytes, at least 95% cardiomyocytes, or at least 99% cardiomyocytes, or any range derivable therein. In yet other embodiments, the selected clonal population of cells may show the ability to differentiate into at least 55% hepatocytes, at least 60% hepatocytes, at least 65% hepatocytes, at least 70% hepatocytes, at least 75% hepatocytes, at least 80% hepatocytes, at least 85% hepatocytes, at least 90% hepatocytes, at least 95% hepatocytes, or at least 99% hepatocytes, or any range derivable therein.

Any method of expanding individualized cells of the population into clonal populations of cells is contemplated for use in the methods set forth herein. The method may involve isolation of individualized cells of the population. Various types of immunoselection may be used in the practice of the present invention to isolate cells, including, but not limited to, flow cytometry (FACS), immunomagnetic techniques, antibody columns, immunoprecipitation, and immunopanning. Additional examples are discussed in the specification below. In particular embodiments, the isolation is performed in vitro. Cell culture techniques are well-known to those of ordinary skill in the art. Non-limiting examples of such techniques are set forth in the specification below.

In some embodiments, the clonal populations of cells are exposed to one or more differentiation agents to induce differentiation into a neural cell type or a cardiomyocyte. The term "inducing differentiation" or "induce differentiation" as used herein is taken to mean causing a stem cell to develop into a specific differentiated cell type as a result of a direct or intentional influence on the stem cell. Influencing factors can include cellular parameters such as ion influx, a pH change and/or extracellular factors, such as secreted proteins, such as but not limited to growth factors and cytokines that regulate and trigger differentiation. It may include culturing the cell to confluence and may be influenced by cell density. In some embodiments, differentiating agents are provided by cells. Non-limiting examples of such agents are set forth in the specification below.

Any method known to those of ordinary skill in the art for assessing differentiation of a cell is contemplated for application in the methods of the present invention. Differentiated cells prepared by exposure of undifferentiated stem cells to the differentiation agent can be characterized morphologically, immunochemically and in other ways to confirm their status as neural precursor cells, cardiomyocytes, hepatocytes, or other cell type. Regarding morphological analysis, cells can be characterized according to a number of phenotypic criteria. The criteria include but are not limited to microscopic observation of morphological features, detection or quantitation of expressed cell markers, enzymatic activity, neurotransmitters and their receptors, and electrophysiological function.

Cells can also be assessed for differentiation according to whether they express phenotypic markers characteristic of particular kinds of cells. Tissue-specific markers known in the art can be detected to assess for differentiation using any suitable immunological technique, such as flow immunocytochemistry and fluorescence activated cell sorting for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Antibody binding to an antigen can be observed by standard immunocytochemistry or flow cytometry assay, after fixation of the cells, using a labeled secondary antibody or other conjugate (such as a biotin-avidin conjugate) to amplify labeling, or other immunological methods well known in the art. In general, the detection of immunocomplex formation is well known in the art and may be achieved through the application of numerous approaches.

In some embodiments, the method for providing a clonal population of cells further includes exposing the cells that have been expanded in vitro to a test compound and measuring a cellular parameter associated with toxicity in the in the expanded cells. In particular embodiments the cells are exposed to the test compound in vitro.

The clonal population of cells may be mammalian cells. Non-limiting examples of sources of cells include mouse, rat, rabbit, dog, cat, sheep, goat, horse, cow, primate, or human. In particular embodiments, the clonal population of cells are human cells.

In certain embodiments, the multipotent or pluripotent cells have been passaged at least once prior to expansion of individualized cells into clonal populations of cells.

The present invention also concerns methods for preparing or producing a clonal population of cells which exhibit improved neural differentiation potential, including the steps of: a) obtaining a population of pluripotent or multipotent cells which have been expanded in vitro and maintained in an undifferentiated or essentially undifferentiated state; b) individualizing and expanding a plurality of cells from a the population of multipotent or pluripotent cells; c) selecting one or more clonal population of cells determined to have the ability to differentiate into a population that is at least about 50% homogeneous for neural cell types; and d) providing cells, or their progeny, of the one or more selected population of cells. The expanded cells may show the ability to differentiate into at least 55% neural cells, at least 60% neural cells, at least 65% neural cells, at least 70% neural cells, at least 75% neural cells, at least 80% neural cells, at least 85% neural cells, at least 90% neural cells, at least 95% neural cells, or at least 99% neural cells, or any range derivable therein. In particular embodiments, the neural cells are dopaminergic cells. The pluripotent or multipotent cells may be any of the cells discussed above. In some embodiments, the method further includes exposing the neural cells to a test compound and measuring a cellular parameter associated with toxicity in the neural cells. Providing cells, or their progeny, may comprise administering the cells, or their progeny, to a subject using any method known to those of ordinary skill in the art.

Some embodiments of the present invention concern a plurality of clonally-derived cardiomyocytes, or a plurality of clonally-derived neural cells produced by the methods of the present invention. The cardiomyocytes or neural cells produced by the methods of the present invention may or may not be comprised in a tissue. The tissue may be in a suitable container means. In particular embodiments, the neural cells are dopaminergic cells. The neural cells may be comprised in a tissue. The tissue and/or cells may be included in a container means.

Further embodiments of the present invention concern compositions that include a plurality of clonally-derived neural cells, hepatocytes, or cardiomyocytes produced by the methods of the present invention, and a carrier. In some embodiments, the plurality of clonally-derived neural cells, hepatocytes, or cardiomyocytes in the composition have been expanded from a single common progenitor cell. In other embodiments, the cells are derived from 2, 3, 4, 5, 6, 7, 8, 9, 10 or more common progenitor cells. The composition may be a pharmaceutical composition, formulated for administration to mammalian subjects.

In some embodiments, the plurality of clonally-derived neural cells, hepatocytes, or cardiomyocytes in the composition are further defined as isolated clonally-derived neural cells or isolated cardiomyocytes. The composition may or may not include other cells that are not isolated clonally-derived neural cells or isolated clonally-derived cardiomyocytes. The number of cells in the composition may be at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, at least $10^{18}$, at least $10^{19}$, at least $10^{20}$ or more cells, or any range of number of cells derivable herein.

In some embodiments, the composition includes at least about 5%, at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more of either neural cells, hepatocytes, or cardiomyocytes in the composition, or any range of percentages derivable herein. In some embodiments, the composition includes about 90% neural cells. In other embodiments, the composition includes at least about 90% cardiomyocytes.

The composition may include any pharmaceutically acceptable carrier known to those of ordinary skill in the art. Non-limiting examples of such carriers are set forth in the specification below. In some embodiments, the composition includes one or more secondary therapeutic agents. Non-limiting examples of secondary therapeutic agents include chemotherapeutic agents. Some examples of chemotherapeutic agents are set forth in the specification below.

The present invention further includes kits that include a suitable container means that includes a plurality of clonally-derived cells produced by methods of the present invention. The cells may or may not be included in a tissue. Other optional kit components are set forth in the specification below.

The present invention also concerns methods of screening test compounds that include: a) contacting a plurality of cardiomyocytes, hepatocytes, or neural cells with the test compound; and, b) determining any change to phenotype or activity of the cells that results from the contact with the test compound, wherein the cells were produced by the methods set forth herein. In some embodiments, the phenotype or activity is a measurement of toxicity. Determining any change to phenotype or activity of the cells may be performed in accordance with any method known to those of ordinary skill in the art. Examples of methods that can be applied include morphological analysis, immunochemical analysis, and other methods set forth above. In some embodiments, the expression of one or more genes is measured in the plurality of cardiomyocytes, hepatocytes, or neural cells. Non-limiting examples of such genes include caspase 3, NF-kB, TNF-alpha, heat-inducible factors (HIF-1 alpha), heat shock proteins (Hsp), a cellular integrity gene (e.g., transaminase), gamma-glutamyl transferase, alkaline phosphatase and oxidative stress genes. Gene expression may be measured using any method or combination of methods well-known to those of ordinary skill in the art. Non-limiting examples of such methods include high throughput gene sequencing, Western blot, Gene expression arrays, flow cytometry, immunofluorescence, promoter/reporter gene based assays, or colorimetric assays. Other examples of parameters that may be measured include contraction of cardiomyocytes, cell death, patterns of action potentials and ion permeability.

Further embodiments of the invention concern methods for preparing or producing a clonal population of cells which exhibit cardiogenic differentiation potential, including the steps of: a) obtaining a population of pluripotent or multipotent cells which have been expanded in vitro and maintained in an undifferentiated or essentially undifferentiated state; b) individualizing a plurality of cells from a the population of multipotent or pluripotent cells and expanding a clonal population of cells; c) selecting one or more clonal population of cells determined to have the ability to differentiate into a population that is at least about 50% homogeneous for cardiomyocytes, and d) using the expanded cells for cell and tissue engineering, drug screening, or cell therapy, based on the ability of the ability of the expanded cells to differentiate into cardiomyocytes as observed in step (c).

Further embodiments of the invention concern methods for providing a clonal population of cells which exhibit hepatocyte differentiation potential, including the steps of: a) obtaining a population of pluripotent or multipotent cells which have been expanded in vitro and maintained in an undifferentiated or essentially undifferentiated state; b) individualizing a plurality of cells from a the population of multipotent or pluripotent cells and expanding a clonal population of cells; c) selecting one or more clonal population of cells determined to have the ability to differentiate into a population that is at least about 50% homogeneous for hepatocytes, and d) using the expanded cells for cell and tissue engineering, drug screening, or cell therapy, based on the ability of the ability of the expanded cells to differentiate into hepatocytes as observed in step (c).

Methods of treating a disease in a subject that involve clonal populations of cells produced by the methods of the present invention are also contemplated. The cells produced by the methods of the present invention or their progeny may be used for transplantation, cell therapy or gene therapy. The present invention contemplates the use of neural cells, hepatocytes, or cardiomyocytes produced by the methods of the present invention for cell-based therapies. For example, the cells may be used to regenerate human tissues that are substantially damaged due to disease or injury is reduced significantly in adults. Regeneration may be performed in vivo or ex vivo. For example, cardiomyocytes produced by the methods set forth herein may be applied in the regeneration of cardiac tissue in a subject where the cardiac tissue of the subject was damaged by cardiac ischemia. Neural cells of the present invention may be administered for the purpose of regenerating cells of the nervous system that have been damaged or that have undergone degeneration. Hepatocytes of the present invention may be administered for the purpose of regenerating cells of the nervous system that have been damaged or that have undergone degeneration. In some embodiments, the cells of the present invention may be directly administered to a subject. Therefore, the methods of the present disclosure may be useful in the treatment of many diseases, injuries, or other detrimental condition of the heart or nervous system.

In some embodiments, cardiomyocytes, hepatocytes, or neural cells of the present invention can be used to modelize human body organs by 3-D reconstruction. For example, for example tissues in the human brain may be modelized by 3-D culturing of neural cells produced by the methods set forth herein. Heart tissue may be derived and reconstructed from cardiomyocytes produced by the methods of the present invention. In some embodiments, the neural cells and cardiomyocytes of the present disclosure may also be used as carrier vehicles for various therapeutically active molecules or genes to be delivered at various sites of the human body, for example by genetically manipulating and differentiating the cells as required, and delivering the cells or tissue to a target site in a donor for gene therapy.

In some embodiments, the method includes administering to a subject a substantially homogeneous population of neural cells; wherein the neural cells were produced by the methods set forth herein or a progeny of neural cells produced by the methods set forth herein. In particular embodiments, the neural cells are dopaminergic cells. In other embodiments, the cells that are administered are cardiomyocytes produced by the methods of the present invention. The subject may be a subject that is known or suspected to have a disease involving the nervous system or a disease involving the cardiovascular system.

In some embodiments, the disease is a neurodegenerative disease. Non-limiting examples of neurodegenerative disease contemplated for treating include Parkinson's disease, Alzeimer disease, multiple sclerosis, stroke, amyotrophic lateral sclerosis (Lou Gehrig's Disease), frontotemporal dementia (Pick's Disease, prion disease, Huntington's disease, cerebral ischemia, idiopathic Morbus Parkinson, topically- or drug-induced Parkinson syndrome, Morbus Alzheimer and cerebral dementia syndromes of different origin, Huntington's chorea, infectious-induced neurodegeneration disorders such as AIDS-encephalopathy, Creutzfeld-Jakob disease, encephalopathies induced by rubiola and herpes viruses and borrelioses, metabolic-toxic neurodegenerative disorders such as hepatic-, alcoholic-, hypoxic-, hypo- or hyperglycemically-induced encephalopathies as well as encephalopathies induced by solvents or pharmaceuticals, degenerative retina disorders of various origin, traumatically-induced brain and bone marrow damage, spinal cord injuries, cerebral hyperexcitability symptoms of varying origin such as after the addition of and/or withdrawal of medicaments, toxins, noxae and drugs, mentally and traumatically-induced cerebral hyperexcitability states, neurodegenerative syndromes of the peripheral nervous system, such as metabolism, medicament, toxically- and infectiously-induced polyneuropathies and polyneuritis. In particular embodiments, the disease is Parkinson's disease. Non-limiting examples of cardiovascular disease include myocardial ischemia, cardiomyopathy, congestive heart failure, and myocardial infarction.

Another aspect of the invention is a method of treating or preventing a cardiac disease or condition. Cardiac disease is typically associated with decreased cardiac function and includes conditions such as, but not limited to, myocardial infarction, cardiac hypertrophy and cardiac arrhythmia. In this aspect of the invention, the method includes introducing an isolated differentiated cardiomyocyte cell of the invention and/or a cell capable of differentiating into a cardiomyocyte cell when treated using a method of the invention into cardiac tissue of a subject. The isolated differentiated cardiomyocyte may be a progeny of a cardiomyotype produced by the methods set forth herein. The isolated cardiomyocyte cell is preferably transplanted into damaged cardiac tissue of a subject. More preferably, the method results in the restoration of cardiac function in a subject. In some embodiments, the subject is a subject with ischemic heart disease or congestive heart failure. The cells may be administered using any method known to those of ordinary skill in the art. Non-limiting examples include intravenous administration, intraarterial administration, and intramyocardiac administration. The method may optionally include performing or administering one or more secondary forms of therapy for the treatment of heart disease. Non-limiting examples of such therapy are discussed below.

In yet another aspect of the invention there is provided a method of repairing cardiac tissue, the method including introducing an isolated cardiomyocyte or cardiac progenitor cell of the invention or a progeny of a cardiomyocyte produced by the methods set forth herein into damaged cardiac tissue of a subject.

Another aspect of the invention is a method of treating or preventing a liver disease or condition. Non-limiting examples of liver disease contemplated for treating include hepatitis, non-alcoholic fatty liver disease, cirrhosis, cancer of the liver, Wilson's disease, primary sclerosing cholangitis, primary biliary cirrhosis, autoimmune disease of small bile ducts, Budd-Chiari syndrome, Gilbert's syndrome, and glycogen storage disease type II.

The cells may be administered using any method known to those of ordinary skill in the art. Non-limiting examples include direct injection, intradermal, intrathecal, intracardiac, transdermal, parenteral, intravenous, intramuscular, intranasal, subcutaneous, injection into the brain or central nervous system, percutaneous, intratracheal, intraperitoneal, perfusion, and lavage. In particular embodiments, Parkinson's disease is treated by injecting dopaminergic neurons into an area include at least a portion of the substantia nigra pars compacta.

Any number of cells known or suspected to be of benefit in treating the disease are administered. In some embodiments, about 100,000 to about 10,000,000 cells are administered per dose. A single dose may be administered, or multiple doses may be administered.

The subject in particular embodiments is a mammalian subject. Non-limiting examples of mammalian subjects include mice, rats, rabbits, dogs, cats, goats, sheep, cows, horses, primates, and humans. In a specific embodiment, the subject is a human.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Any embodiment of any of the present methods, cells, and kits may consist of or consist essentially of—rather than comprise/include/contain/have the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

(FIG. 1A) Flow cytometric analysis of nestin and beta-III-tubulin expression during early differentiation. (FIG. 1B) Flow cytometric analysis of nestin and Oct-4 expression during early differentiation. (FIG. 1C) Analysis of CFSE dilution by flow cytometry during early and late differentiation of ESC. (FIG. 1D) Combination of phenotypic and CFSE dilution analysis in differentiating ESC. The CFSE dilution was assessed at different time points for different subpopulations: nestin-positive/beta-III-tubulin-negative (neuroepithelial cells), nestin-negative/beta-III-tubulin-positive (neuronal cells), nestin-negative/beta-Ill-tubulin-negative (non-neural cells).

(FIG. 2A)—In an experimental setup where one colony was derived from one parental ESC, cells were stained for nestin and beta-III-tubulin after 72 h differentiation. (FIG. 2B) ESC-Talpha-1-GFP were submitted to neural differentiation for 72 h and analyzed for green fluorescence. (FIG. 2C) 150 ESC-derived colonies were analyzed for the presence or not of NeuN-positive (mature-stage neurons), TH-positive (dopaminergic neurons) and beta-III-tubulin-positive (neuronal cells) cells. (FIG. 2D), (FIG. 2E) ESC-H2B-mRFP1 were submitted to neural differentiation and monitored by live imaging during the first two days.

(FIG. 3B)—The expression of 6800 genes varied significantly between ESC clones. Based on gene expression profile of each clone, a hierarchical cluster was established to classify ESC clones. The two most different clones were clones 1 and 2 whereas clones 4 and 6 were highly similar.

(FIG. 4A, FIG. 4B, FIG. 4C)— Clonal ESCs were submitted to neural differentiation by co-culture on PA6 stromal cells. (FIG. 4A) The percentage of colonies including nestin-positive neuroepithelial cells was evaluated after 3 days. (FIG. 4B, FIG. 4C) The percentage of colonies including beta-III-tubulin-positive neuronal cells (FIG. 4B) or (C) TH-positive dopaminergic neurons was evaluated after 1 week. (FIG. 4D) ESC clones 1, 2, 3, and 4 were differentiated towards embryoid bodies. Cardiac differentiation was evaluated by the percentage of beating embryoid bodies at different time points.

(FIG. 6B)—D3 sublines were submitted to neural differentiation by co-culture on PA6 stromal cells. The percentage of colonies including βIII-tubulin+ neuronal cells), neuN+ mature neurons and TH+ dopaminergic neurons was evaluated after 1 week.

(FIG. 7A) Immunofluorescence against nestin and (FIG. 7B) beta-III-tubulin in neural cells after one week neural differentiation of ESC-H2B-mRFP1-βIIIp-GFP on PA6 stroma cells.

DESCRIPTION OF ILLUSTRATIVE EMBODIMENTS

Figure 1:
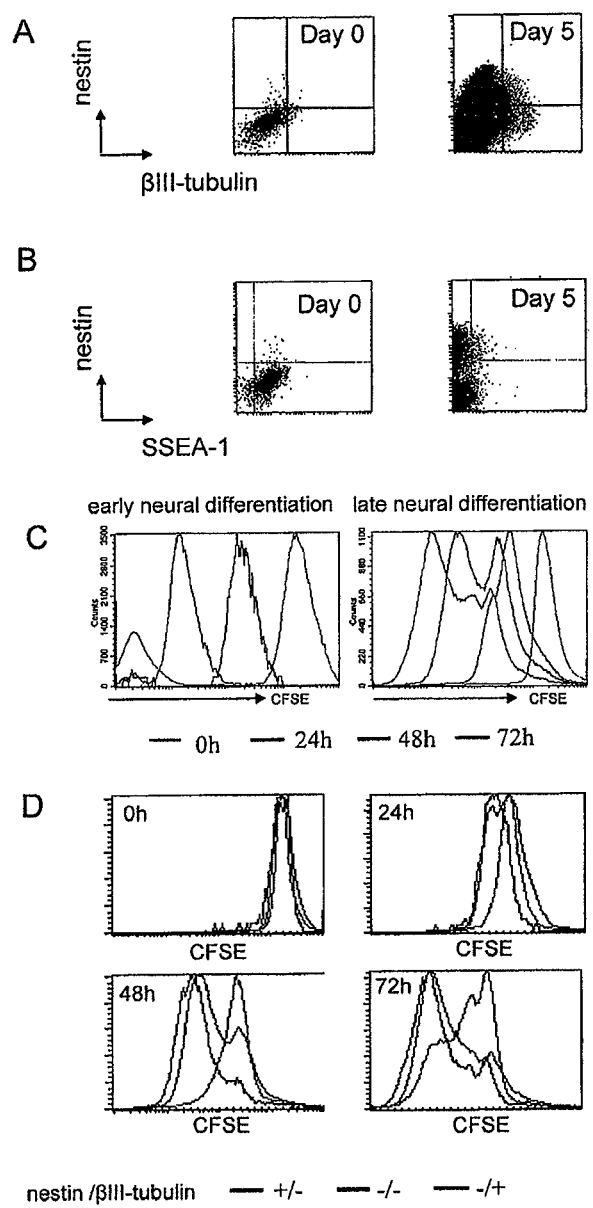
FIGS. 1A-D. A subpopulation of ESC escapes neural differentiation. ESCs were subjected to neural differentiation by 5 days of coculture with PA6 stromal cells. Early differentiation was performed during the first 5 days. Late differentiation was induced after cell dissociation and re-plating on polyornithine.

The present invention includes a controlled differentiation process of neural cells and cardiomyocytes from pluripotent and multipotent stem cells, resulting in reduced heterogeneity of the resulting cell population. Heterogeneity of cells that have differentiated from pluripotent stem cells impairs the quality and purity of cell preparations for therapeutic applications, and is potentially dangerous to the recipient subject. As shown in the below examples, clonal ESC sublines expressing markers of inner cell mass (ICM) and pluripotency were established, and certain clonal sublines were observed to display distinct differentiation potentials that were stable over time. For example, various clonal pluripotent stem cell lines were established which exhibit preferential differentiation into ectoderm (e.g., neuronal), endoderm (e.g., hepatocytes), or mesoderm (e.g., muscle cell or cardioyocyte) cell lineages. Induced pluripotent stem cells (iPS), including as iPS cells that are presently available and/or iPS that may be developed in the future, or ESC may be used to produce a clonal pluripotent stem cell line exhibiting an altered differentiation potential. Thus, the present invention in part provides for methods of providing a clonal population of cells that have reduced heterogeneity and thus greater potential for therapeutic effect with reduced potential for side effects. In various embodiments, cells derived from a clonal pluripotent cell line produced via the methods described herein may be used for pharmacological or toxicological evaluation of a test compound.

A. Pluripotent and Multipotent Cells

Methods of providing clonal populations of cells from a population of pluripotent or multipotent cells are contemplated by the present invention. Any pluripotent or multipotent cell is contemplated for use in the present methods. Non-limiting examples of pluripotent stem cells and multipotent stem cells are discussed below.

1. Mammalian Embryonic Stem Cells

Mammalian embryonic stem (ES) cells are pluripotent cells derived from the inner cell mass of a blastocyst. ES cells can be isolated by removing the outer trophectoderm layer of a developing embryo, then culturing the inner mass cells on a feeder layer of non-growing cells. Under appropriate conditions, colonies of proliferating, undifferentiated ES cells are produced. The colonies can be removed, dissociated into individual cells, then replated on a fresh feeder layer. The replated cells can continue to proliferate, producing new colonies of undifferentiated ES cells. The new colonies can then be removed, dissociated, replated again and allowed to grow. This process of "subculturing" or "passaging" undifferentiated ES cells can be repeated a number of times to produce cell lines containing undifferentiated ES cells (U.S. Pat. Nos. 5,843,780; 6,200,806; 7,029,913). A "primary cell culture" is a culture of cells directly obtained from a tissue such as the inner cell mass of a blastocyst. A "subculture" is any culture derived from the primary cell culture.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al, 2000.) In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thompson et al. In addition, subclones H9.1 and H9.2 of the H9 line have been developed. It is anticipated that virtually any ES or stem cell line known in the art and may be used with the present invention, such as, e.g., those described in Yu and Thompson (2008), which is incorporated herein by reference. Additional iPS cells may be established from a subject to produce cells which may be therapeutically administered back into the patient. iPS cells may thus be used for personalized medicine.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

A pluripotent cell is capable of differentiating into any cell of the body. The pluripotency of ES cells has been determined in various ways (Martin, 1982). In one test, mouse ES cells derived from the inner cell mass of a blastocyst are injected into the cavity of another blastocyst. The injected blastocyst is deposited into the uterus of a pseudopregnant female mouse to produce progeny that are chimeras of injected and recipient blastocyst cells. In another test, mouse ES cells are injected into adult mice to produce tumors called teratomas. Such tumors can contain a variety of cell types derived from endoderm, mesoderm, and ectoderm. In certain embodiments, one or more teratoma-derived cells may be cultured or differentiated into neural or neural-committed cells according to the present invention. The pluripotency of human ES cells can also be tested by the formation of teratomas in immunodeficient mice. A third test is to alter culture conditions to allow ES cells to differentiate into more specialized cells. For example, mouse ES cells can spontaneously differentiate into various cell types by removing the feeder layer and adding LIF to the culture medium. Similarly, human ES cells can spontaneously differentiate by removing the feeder layer and growing the ES cells on a non-adherent surface in suspension (Itskovitz-Eldor et al., 2000; Reubinoff et al., 2000; Roach et al., 1993). Under such conditions, the ES cells can form cell aggregates called embryoid bodies which contain cells having characteristics of neurons and heart muscle cells. In all of these tests, the pluripotency of ES cells is shown by their ability to generate cells of endoderm, mesoderm, and ectoderm origin.

ES cells can be characterized by the proteins they produce. For example, the following marker proteins have been used to characterize ES cells: stage-specific embryonic antigen SSEA-1, stage-specific embryonic antigen SSEA-3, stage-specific embryonic antigen SSEA-4, tumor rejection antigen-1-60 (TRA1-60), tumor rejection antigen-1-81 (TRA1-81), alkaline phosphatase (AP), and transcription factor Oct-4. As shown in Table 1, mouse, human and primate cells differ in their pattern of expression of these markers. For example, SSEA-1 is expressed in mouse ES cells, but not human or monkey ES cells, while TRA1-60 is expressed in human and monkey ES cells but not mouse ES cells.

TABLE 1

ES Cell Marker Expression

| Marker | Mouse | Human | Monkey |
| --- | --- | --- | --- |
| SSEA-1 | Yes | No | No |
| SSEA-2 | No | Yes | Yes |
| SSEQ-3 | No | Yes | Yes |
| TRA1-60 | No | Yes | Yes |
| TRA1-81 | No | Yes | Yes |
| AP | Yes | Yes | Yes |
| Oct-4 | Yes | Yes | Yes |

Depending on culture conditions, ES cells can produce colonies of differentiated cells or undifferentiated cells. The term "differentiate" means the progression of a cell down a developmental pathway. The term "differentiated" is a relative term describing a cell's progression down a developmental pathway in comparison with another cell. For example, a pluripotent cell can give rise to any cell of the body, while a more differentiated cell such a hematopoetic cell will give rise to fewer cell types. As used herein, "undifferentiated ES cells" refers to ES cells that do not show the characteristics of more specialized cells.

2. Induced Pluripotent Stem Cells

Induced pluripotent stem (iPS) cells are cells which have the characteristics of ES cells but are obtained by the reprogramming of differentiated somatic cells. Induced pluripotent stem cells have been obtained by various methods. In one method, adult human dermal fibroblasts are transfected with transcription factors Oct3/4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF. Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having neuronal structures and neuronal markers. It is anticipated that virtually any iPS cells or cell lines may be used with the present invention, including, e.g., those described in Yu and Thompson (2008).

In another method, human fetal or newborn fibroblasts are transfected with four genes, Oct4, Sox2, Nanog and Lin28 using lentiviral transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage and gut epithelium after injection into mice.

Methods of preparing induced pluripotent stem cells from mouse are also known (Takahashi and Yamanaka, 2006). Induction of iPS cells typically require the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf4 and, optionally, c-Myc. In various embodiments, Oct-4, Nanog, Klf-4, and Sox-2, may be used to induce and/or maintain pluripotency of ESC.

3. Embryonic Stem Cells Derived by Somatic Cell Nuclear Transfer

In certain embodiments, the pluripotent stem cell is an embryonic stem cell derived by somatic cell nuclear transfer. In somatic cell nuclear transfer, a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo. As used herein, the term "ES cells" refers to embryonic stem cells derived from embryos containing fertilized nuclei. ES cells are distinguished from embryonic stem cells produced by nuclear transfer, which are referred to as "embryonic stem cells derived by somatic cell nuclear transfer."

4. Neural Stem Cells

Neural stem cells are undifferentiated cells from neural tissue that are capable of giving rise to neural stem cells (capable of self-renewal) or to cells that will terminally differentiate into neural cells. A neural stem cell can be an adult neural stem cell or an embryonic neural stem cell. As used herein, the term "adult" neural stem cell refers to stem cells derived from somatic tissue whether from an adult or a child. Methods for isolating adult and embryonic neural stem cells from humans and other animals are well known (Rietze and Reynolds, 2006; Svendsen et al., 1999).

B. Cell Culture

1. Cell Culture Generally

Any method of culturing pluripotent stem cells and multipotent stem cells known to those of ordinary skill in the art is contemplated for inclusion in the methods of the present invention. standard textbooks and reviews in cell biology, tissue culture, and embryology, including Teratocarcinomas and embryonic stem cells: A practical approach (1987); Guide to Techniques in Mouse Development (1993); Embryonic Stem Cell Differentiation In Vitro (1993); Properties and uses of Embryonic Stem Cells: Prospects for Application to Human Biology and Gene Therapy (1998), all incorporated herein by reference.

Standard methods used in tissue culture generally are described in Animal Cell Culture (1987); Gene Transfer Vectors for Mammalian Cells (1987); and Current Protocols in Molecular Biology and Short Protocols in Molecular Biology (1987 & 1995).

2. Growth Media

A variety of media an culture conditions for stem cell culture are known in the art. In certain aspects, cells may be grown with feeder cells such a fibroblasts or in fibroblast conditioned media. However, in some instances it may be preferred that stem cells are grown in the absence of feeder cells. In some aspects, cells may be grown in a defined media such as TeSR (e.g., MTESR™1 available from BD Biosciences) (Ludwig et al., 2006a, U.S. Application 2006/0084168). Such media may be used for serum free culture of ES cells. In some embodiments, media is supplemented with bovine or human serum to supply the necessary growth factors (Ludwig et al., 2006b).

For example, the culture medium can be DMEM, RPMI 1640, GMEM, or neurobasal medium. The culture medium can contain serum, or can be a serum-free medium. The serum-free medium can be used without the addition of an exogenous growth factor, or can be supplemented with a growth factor such as basic fibroblast growth factor (bFGF), insulin-like growth factor-2 (IGF-2), epidermal growth factor (EGF), fibroblast growth factor 8 (FGF8), Sonic hedgehog (Shh), brain derived neurotrophic factor (BDNF), glial cell line-derived neurotrophic factor (GDNF), or Vitamin C. The non-adherent surface can be low-attachment tissue culture plastic.

As in the first step, the culture medium of the second step can be any medium that supports the growth of pluripotent stem cells or neural stem cells. The medium can contain serum, or can be a serum-free medium with or without the addition of a growth factor. Similarly, the cells can be grown in suspension on a non-adherent tissue culture surface.

In still further aspects of the invention additional media components may be included in stem cell growth media such as molecules that reduce stem cell apoptosis when cells become disassociated (e.g., during splitting of cell populations). For example, media may comprise one or more Rho-associated kinase (ROCK) inhibitor such a Y-27632 or a derivative thereof. In some aspects, media of the invention may comprise HA-100: or a derivative thereof. Other ROCK inhibitors which may be included in a stem cell growth media include H-1152 ((S)-(+)-2-Methyl-1-[(4-methyl-5-isoquinolinyl)sulfonyl]homopiperazine). H-1152 exhibits an approximately ten-fold greater potency than HA-100. Thus, H-1152 may be present in an ES cell growth media, e.g., at a concentration of about 0.1-10 µM, about 0.5-5 µM, about 1-3 µM, or about 0.5, 0.6, 0.7, 0.8, 0.9, 1, 2, 3, 4, or 5 µM, or any range derivable therein. In certain embodiments HA-100 is present in an ES cell growth media at about 1 µM. H-1152, which allows for very efficient seeding of individualized human ES cells in 96-well plates (similar to HA-100 but at 10-fold lower concentration). Individualized HES cells that are otherwise passaged in cell clumps allow more uniform cell densities per well, which is a stringent prerequisite for cell-based small molecule screening. H-1152 can thus be used in protocols for ES cell-based small molecule screening which involve automated cell culture according to the present invention. H-1152 has been previously described in, e.g., Ikenoya et al. (2002) and Sasaki et al. (2002), which are incorporated herein by reference.

Other ROCK inhibitors which may be included in an ES cell growth media include Y-27632, N-(4-Pyridyl)-N'-(2,4, 6-trichlorophenyl)urea, 3-(4-Pyridyl)-1H-indole, glycyl-H1152 ((S)-(+)-2-Methyl-4-glycyl-1-(4-methylisoquinolinyl-5-sulfonyl)homopipera-zine) and/or HA1100 (Hydroxyfausdil). Y-27632 ((R)-(+)-trans-4-(1-Aminoethyl)-N-(4-Pyridyl)cyclohexanecarboxamide) is commercially available from Sigma-Aldrich and has been described previously (see, e.g., Maekawa et al., 1999; Davies et al., 2000).

3. Cell Culture Apparatus, Systems and Methods

In some aspects, the present invention may take advantage of bioreactor technology. Growing cells in a bioreactor allows for large scale production of fully biologically-active cells capable of further differentiation for end use. Bioreactors have been widely used for the production of biological products from both suspension and anchorage dependent animal cell cultures. Microcarrier cell culture in stirred tank bioreactor provides very high volume-specific culture surface area and has been used for the production of viral vaccines (Griffiths, 1986). Furthermore, stirred tank bioreactors have industrially been proven to be scaleable, however such technologies may only be employed when cells may be grown in anchorage independent cultures. The multiplate CELLCUBE™ cell culture system manufactured by Corning-Costar also offers a very high volume-specific culture surface area. Cells grow on both sides of the culture plates hermetically sealed together in the shape of a compact cube. Unlike stirred tank bioreactors, the CELLCUBE™ culture unit is disposable. This is very desirable at the early stage production of clinical product because of the reduced capital expenditure, quality control and quality assurance costs associated with disposable systems.

a. Non-Perfused Attachment Systems

Traditionally, anchorage-dependent cell cultures are propagated on the bottom of small glass or plastic vessels as described herein. The restricted surface-to-volume ratio offered by classical and traditional techniques, suitable for the laboratory scale, has created a bottleneck in the production of cells and cell products on a large scale. In an attempt to provide systems that offer large accessible surfaces for cell growth in small culture volume, a number of techniques have been proposed: the roller bottle system, the stack plates propagator, the spiral film bottle system, the hollow fiber system, the packed bed, the plate exchanger system, and the membrane tubing reel. Since these systems are non-homogeneous in their nature, and are sometimes based on multiple processes, they suffer from the following shortcomings—limited potential for scale-up, difficulties in taking cell samples, limited potential for measuring and controlling key process parameters and difficulty in maintaining homogeneous environmental conditions throughout the culture.

Despite these drawbacks, a commonly used process for large scale anchorage-dependent cell production is the roller bottle. Being little more than a large, differently shaped T-flask, simplicity of the system makes it very dependable and, hence, attractive. Fully automated robots are available that can handle thousands of roller bottles per day, thus eliminating the risk of contamination and inconsistency associated with the otherwise required intense human handling.

b. Cultures on Microcarriers

In an effort to overcome the shortcomings of the traditional anchorage-dependent culture processes, van Wezel (1967) developed the concept of the microcarrier culturing systems. In this system, cells are propagated on the surface of small solid particles suspended in the growth medium by slow agitation. Cells attach to the microcarriers and grow gradually to confluency on the microcarrier surface. In fact, this large scale culture system upgrades the attachment dependent culture from a single disc process to a unit process in which both monolayer and suspension culture have been brought together. Thus, combining the necessary surface for a cell to grow with the advantages of the homogeneous suspension culture increases production.

The advantages of microcarrier cultures over most other anchorage-dependent, large-scale cultivation methods are several fold. First, microcarrier cultures offer a high surface-to-volume ratio (variable by changing the carrier concentration) which leads to high cell density yields and a potential for obtaining highly concentrated cell products. Cell yields are up to $1-2*10^7$ cells/ml when cultures are propagated in a perfused reactor mode. Second, cells can be propagated in one unit process vessels instead of using many small low-productivity vessels (i.e., flasks or dishes). This results in far better nutrient utilization and a considerable saving of culture medium. Moreover, propagation in a single reactor leads to reduction in need for facility space and in the number of handling steps required per cell, thus reducing labor cost and risk of contamination. Third, the well-mixed and homogeneous microcarrier suspension culture makes it possible to monitor and control environmental conditions (e.g., pH, $pO_2$, and concentration of medium components), thus leading to more reproducible cell propagation and product recovery. Fourth, it is possible to take a representative sample for microscopic observation, chemical testing, or enumeration. Fifth, since microcarriers settle out of suspension quickly, use of a fed-batch process or harvesting of cells can be done relatively easily. Sixth, the mode of the anchorage-dependent culture propagation on the microcarriers makes it possible to use this system for other cellular manipulations, such as cell transfer without the use of proteolytic enzymes, cocultivation of cells, transplantation into animals, and perfusion of the culture using decanters, columns, fluidized beds, or hollow fibers for microcarrier retainment. Seventh, microcarrier cultures are relatively easily scaled up using conventional equipment used for cultivation of microbial and animal cells in suspension.

c. Microencapsulation of Mammalian Cells

One method which has shown to be particularly useful for culturing mammalian cells is microencapsulation. The mammalian cells are retained inside a semi-permeable hydrogel membrane. A porous membrane is formed around the cells permitting the exchange of nutrients, gases, and metabolic products with the bulk medium surrounding the capsule. Several methods have been developed that are gentle, rapid and non-toxic and where the resulting membrane is sufficiently porous and strong to sustain the growing cell mass throughout the term of the culture. These methods are all based on soluble alginate gelled by droplet contact with a calcium-containing solution. Lim (1982, U.S. Pat. No. 4,352,883, incorporated herein by reference) describes cells concentrated in an approximately 1% solution of sodium alginate which are forced through a small orifice, forming droplets, and breaking free into an approximately 1% calcium chloride solution. The droplets are then cast in a layer of polyamino acid that ionically bonds to the surface alginate. Finally the alginate is reliquefied by treating the droplet in a chelating agent to remove the calcium ions. Other methods use cells in a calcium solution to be dropped into a alginate solution, thus creating a hollow alginate sphere. A similar approach involves cells in a chitosan solution dropped into alginate, also creating hollow spheres.

Microencapsulated cells are easily propagated in stirred tank reactors and, with beads sizes in the range of 150-1500 µm in diameter, are easily retained in a perfused reactor using a fine-meshed screen. The ratio of capsule volume to total media volume can be maintained from as dense as 1:2 to 1:10. With intracapsular cell densities of up to $10^8$, the effective cell density in the culture is $1-5*10^7$.

The advantages of micro encapsulation over other processes include the protection from the deleterious effects of shear stresses which occur from sparging and agitation, the ability to easily retain beads for the purpose of using perfused systems, scale up is relatively straightforward and the ability to use the beads for implantation.

d. Perfused Attachment Systems

Perfused attachment systems are also contemplated for use in the methods of the present invention. Perfusion refers to continuous flow at a steady rate, through or over a population of cells (of a physiological nutrient solution). It implies the retention of the cells within the culture unit as opposed to continuous-flow culture which washes the cells out with the withdrawn media (e.g., chemostat). The idea of perfusion has been known since the beginning of the century, and has been applied to keep small pieces of tissue viable for extended microscopic observation. The technique was initiated to mimic the cells milieu in vivo where cells are continuously supplied with blood, lymph, or other body fluids. Without perfusion, cells in culture go through alternating phases of being fed and starved, thus limiting full expression of their growth and metabolic potential.

The current use of perfused culture is in response to the challenge of growing cells at high densities (i.e., $0.1-5*10^8$ cells/ml). In order to increase densities beyond $2-4*10^6$ cells/ml, the medium has to be constantly replaced with a fresh supply in order to make up for nutritional deficiencies and to remove toxic products. Perfusion allows for a far better control of the culture environment (pH, $pO_2$, nutrient levels, etc.) and is a means of significantly increasing the utilization of the surface area within a culture for cell attachment.

The development of a perfused packed-bed reactor using a bed matrix of a non-woven fabric has provided a means for maintaining a perfusion culture at densities exceeding $10^8$ cells/ml of the bed volume (CELLIGEN™, New Brunswick Scientific, Edison, N.J.). Briefly described, this reactor comprises an improved reactor for culturing of both anchorage- and non-anchorage-dependent cells. The reactor is designed as a packed bed with a means to provide internal recirculation. Preferably, a fiber matrix carrier is placed in a basket within the reactor vessel. A top and bottom portion of the basket has holes, allowing the medium to flow through the basket. A specially designed impeller provides recirculation of the medium through the space occupied by the fiber matrix for assuring a uniform supply of nutrient and the removal of wastes. This simultaneously assures that a negligible amount of the total cell mass is suspended in the medium. The combination of the basket and the recirculation also provides a bubble-free flow of oxygenated medium through the fiber matrix. The fiber matrix is a non-woven fabric having a "pore" diameter of from 10 µm to 100 µm, providing for a high internal volume with pore volumes corresponding to 1 to 20 times the volumes of individual cells.

In comparison to other culturing systems, this approach offers several significant advantages. With a fiber matrix carrier, the cells are protected against mechanical stress from agitation and foaming. The free medium flow through the basket provides the cells with optimum regulated levels of oxygen, pH, and nutrients. Products can be continuously removed from the culture and the harvested products are free of cells and can be produced in low-protein medium which facilitates subsequent purification steps. Also, the unique design of this reactor system offers an easier way to scale up the reactor. Currently, sizes up to 30 liter are available. One hundred liter and 300 liter versions are in development and theoretical calculations support up to a 1000 liter reactor. This technology is explained in detail in WO 94/17178 (Aug. 4, 1994, Freedman et al.), which is hereby incorporated by reference in its entirety.

The CELLCUBE™ (Corning-Costar) module provides a large styrenic surface area for the immobilization and growth of substrate attached cells. It is an integrally encapsulated sterile single-use device that has a series of parallel culture plate joined to create thin sealed laminar flow spaces between adjacent plates.

The CELLCUBE™ module has inlet and outlet ports that are diagonally opposite each other and help regulate the flow of media. During the first few days of growth the culture is generally satisfied by the media contained within the system after initial seeding. The amount of time between the initial seeding and the start of the media perfusion is dependent on the density of cells in the seeding inoculum and the cell growth rate. The measurement of nutrient concentration in the circulating media is a good indicator of the status of the culture. When establishing a procedure it may be necessary to monitor the nutrients composition at a variety of different perfusion rates to determine the most economical and productive operating parameters.

Cells within the system reach a higher density of solution (cells/ml) than in traditional culture systems. Many typically used basal media are designed to support $1-2*10^6$ cells/ml/day. A typical CELLCUBE™, run with an 85,000 cm² surface, contains approximately 6 L media within the module. The cell density often exceeds $10^7$ cells/mL in the culture vessel. At confluence, 2-4 reactor volumes of media are required per day.

e. Apparatus/Systems for Automated Expansion of ES Cells

Certain aspects of the invention involve apparatus or systems for automated expansion of pluripotent or multipotent cells, such as ES cells. An exemplary device can comprise a viable ES cell population, a liquid handler unit in fluid communication with an incubator and a controller comprising an operating program for cell separation.

ES cell populations for use in an apparatus of the invention may comprise an ES cell population from any source known to those of skill in the art. For instance, methods for obtaining embryonic stem cells, such as human ESCs have been previously described in U.S. Pat. Nos. 5,843,780, 6,200,806 and 7,029,913. It is understood that the term apparatus as used herein is not limited to devices in a single housing, and may include multiple devices linked together, for example, via electrical, mechanical, or other coupling mechanisms.

Various types of liquid handler units are commercially available, for example in certain aspects, a liquid handler may be a robotic handler such as a Hamilton MICROLAB® STAR work station or a Beckman Coulter BIOMEK® 2000 liquid handler (B2K). See also, U.S. Pat. No. 6,325,114 concerning robotic liquid handlers. In still other aspects, a liquid handler maybe a device that does not comprise a robotic arm but rather moves liquid by actuation of valves and the application of pressure gradients, such as a fluidic or microfluidic liquid handler.

A wide array of incubators are known in the art and may be used according to embodiments of the invention. For example, in certain embodiments an incubator may be a Kendro CYTOMAT™ incubator.

Furthermore, cell expansion apparatus and systems in certain embodiments of the invention may comprise a controller for the control of stemcell expansion. Such a program may be in electronic communication with liquid handler unit, a fluid communication device and/or an incubator. The skilled artisan will recognize that in certain aspects, an operating apparatus or system may be comprised in a computer or a computer-readable medium.

As will be appreciated, the operating apparatus may be effected by means of computer automation, whereby the operating apparatus directs and controls the various hardware devices that make up certain embodiments of the present invention. An exemplary operating program that may be employed to effect integration of hardware elements is the OVERLORD™ Integration software program (Biosero, Inc.), which employs a simple drag-and-drop system for setting up communication between instruments. The software also permits a range of programming elements such as numeric and string variables, conditional statements, and control loops.

Optionally, an apparatus according to the invention may comprise fluid communication device that facilitates fluid communication between incubator and liquid handler unit. For example, in the case where a liquid handler is a robotic handler, fluid communication device may be a robotic device, such as a device that moves plates of cells between a liquid handler unit and an incubator. For example, a robotic device may be a Hudson Platecrane XL.

Furthermore, a pluripotent or ES cell expansion system may comprise one or more reservoirs that comprise reagent for the liquid handler unit. For example, reservoirs may comprise: cell growth media with or without a proteinase inhibitor; cell culture plates; a proteolytic enzyme solution; phosphate buffered saline (PBS); and/or pipette tips. In certain aspects, additional robotic devices may be used to facilitate communication between a liquid handler device and a reservoir. In certain embodiments a reservoir may contain a TeSR media, optionally with a ROCK inhibitor and/or a protease inhibitor such as a soybean trypsin inhibitor. In other embodiments, the reservoir may contain a solution comprising a proteolytic enzyme (e.g., trypsin, EDTA, etc.).

In some aspects a Beckman Coulter Stacker Carousel may be used to facilitate communication between a reservoir (e.g., a plate or pipette reservoir) and a liquid handler device.

The reservoirs may be housed in a temperature control unit, such as a refrigerator. The temperature control unit may optionally comprise a heating unit to pre-heat solutions to a desired temperature (e.g., about 37° C.); however, the inventors have discovered that a heating unit is not necessary in certain embodiments, as a simple refrigerator.

4. Isolation of Individual Cells from a Population

Certain embodiments of the methods of the present invention involve the selection of a cell from a population of cells. Any method known to those of ordinary skill in the art is contemplated as a method for isolating an individual cell from a population of cells. In some embodiments, a classical limit dilution assay using a flow cytometry cell sorter (in 96 well plates) is utilized to isolate individual cells from a population.

Many cell sorting techniques are available for sorting cardiomyocyte-lineage cells from non-cariomyocyte-lineage cells. Those cell sorting techniques include, but are not limited to negative immunoselection and positive immunoselection.

Immunoselection is a generic term that encompasses a variety of techniques in which the specificity of a selection system is conferred by an antibody or an antibody-like molecule such as a lectin or hapten. An example of such specificity is the affinity of an antibody for a specific cell surface antigen. Two general types of immunoselection techniques are practiced. Negative immunoselection involves the elimination of a specific subpopulation of components from a heterogeneous population such as the elimination on non-cardiomyocyte-lineage cells from the cell population that results from the differentiation of primate pluripotent stem cells according to the methods herein. In contrast, positive immunoselection refers to the direct selection and recovery of a specific component, such as the direct selection and recovery of cardiomyocyte-lineage cells from the differentiation of primate pluripotent stem cells according to the methods herein. Various types of immunoselection may be used in the practice of the present invention, including, but not limited to, flow cytometry (FACS), immunomagnetic techniques, antibody columns, immunoprecipitation, and immunopanning.

5. Maintenance of an Undifferentiated State

Pluripotent and multipotent cells can be maintained in an undifferentiated state by any method known to those of ordinary skill in the art. For example, an undifferentiated state may be maintained by culturing the cells in the presence of serum and a feeder layer. For example, the feeder lay may be mouse embryonic fibroblasts. Other methods for maintaining stem cells in an undifferentiated state are also known. For example, mouse ES cells can be maintained in an undifferentiated state by culturing in the presence of LIF without a feeder layer. However, unlike mouse ES cells, human ES cells do not respond to LIF. Human ES cells can be maintained in an undifferentiated state by culturing ES cells on a feeder layer of fibroblasts in the presence of basic fibroblast growth factor (Amit et al., 2000), or by culturing on a protein matrix, such as Matrigel or laminin, without a feeder layer and in the presence of fibroblast-conditioned medium plus basic fibroblast growth factor, (Xu et al., 2001; U.S. Pat. No. 6,833,269).

Cultures of pluripotent or multipotent cells are described as "undifferentiated" when a substantial proportion of stem cells and their derivatives in the population display morphological characteristics of undifferentiated cells, clearly distinguishing them from differentiated cells of embryo or adult origin. Undifferentiated ES cells are recognized by those skilled in the art, and typically appear in the two dimensions of a microscopic view in colonies of cells with high nuclear/cytoplasmic ratios and prominent nucleoli. It is understood that colonies of undifferentiated cells can have neighboring cells that are differentiated.

C. Differentiation of Stem Cells

The stem cell, such as a human embryonic stem cell (hES), and any cell preferably providing differentiating factor(s) are co-cultured in vitro. This involves introducing the hES cells preferably to an embryonic cell monolayer produced by proliferation of the embryonic cell in culture. The embryonic cell monolayer may be grown to substantial confluence and the stem cell is allowed to grow in the presence of extracellular medium of the embryonic cells for a period of time sufficient to induce differentiation of the stem cell to a specific cell type. Alternatively, the stem cell may be allowed to grow in culture containing the extracellular medium of the embryonic cell(s), but not in the presence of the embryonic cell(s). The embryonic cells and stem cells may be separated from each other by a filter or an acellular matrix such as agar.

For differentiation of stem cells, the stem cell may be plated on a monolayer of embryonic cells and allowed to grow in culture to induce differentiation of the stem cell. However, for the purposes of this invention, stem cells may be differentiated to cardiomyocytes and cardiac progenitors by any method known to those of ordinary skill in the art. For example, ascorbic acid can be added to enhance the differentiation.

A gradual withdrawal from optimal conditions for stem cell growth promotes differentiation of the stem cell to specific cell types. Suitable culture conditions may include the addition of DMSO, retinoic acid, FGFs or BMPs in co-culture which could increase differentiation rate and/or efficiency.

The cell density of the embryonic cell layer typically affects its stability and performance. A cell culture media for enhancing cardiomyocyte differentiation of a hES cell said culture media may include ascorbic acid, or a derivative or functional equivalent thereof. The concentration of the media is preferably of a suitable concentration to deliver ascorbic acid, a derivative or functional equivalent thereof to the hES cells. The concentration may range from $10^{-3}$M to $10^{-5}$M. More preferably the concentration is $10^{-4}$M. Any type of culture media is suitable providing it is suitable for culturing hES cells.

The cell culture media may be serum free. However, various concentrations of serum may be tolerated and may range from 20% to 0%. The serum concentrations may also be provided at a concentration selected from the group including 20%, 10%, 5%, 2.5% and 0%.

In accordance with the present invention, exposure of undifferentiated mammalian stem cells to a differentiation agent is performed. The undifferentiated stem cells can be cultured for a time in the presence of the differentiation agent, then allowed to proliferate in the absence of the differentiation agent. Variations of this basic procedure are contemplated so long as the result of exposure to the differentiation agent is the differentiation of stem cells to neural cells, hepatocytes, or cardiomyocytes. For example, in a first step, undifferentiated stem cells can be cultured in suspension on a non-adherent surface in the presence of the differentiation agent. In a second step, after exposure of the stem cells to the differentiation agent for an appropriate amount time, the cells can be cultured in suspension on a non-adherent surface in the presence of the differentiation agent, with fresh culture medium. In a third step, the exposed cells can be plated and grown in the absence of the differentiation agent. Proliferating cells can be split and passaged when the cells reach about 80-90% confluency.

In the first step, the culture medium can be any medium that supports the survival and growth of stem cells. For example, the culture medium can be DMEM, RPMI 1640, GMEM, or neurobasal medium. The culture medium can contain serum, or can be a serum-free medium. The serum-free medium can be used without the addition of an exogenous growth factor, or can be supplemented with a growth factor such as basic fibroblast growth factor (bFGF), insulin-like growth factor-2 (IGF-2), epidermal growth factor (EGF), fibroblast growth factor 8 (FGF8), Sonic hedgehog (Shh), brain derived neurotrophic factor (BDNF), glial cell line-derived neurotrophic factor (GDNF), or Vitamin C. The non-adherent surface can be low-attachment tissue culture plastic.

As in the first step, the culture medium of the second step can be any medium that supports the growth of stem cells. The medium can contain serum, or can be a serum-free medium with or without the addition of a growth factor. Similarly, the cells can be grown in suspension on a non-adherent tissue culture surface.

In the third step, exposed cells can be plated on an adherent surface in culture medium containing serum, in serum-free culture medium without a growth factor, or in serum-free culture medium containing a growth factor such as bFGF, IGF-2, EGF, FGF8, Shh, BDNF, GDNF, or Vitamin C. The adherent surface can be tissue culture plastic, or can be a coated tissue culture surface such as a tissue culture plate coated with polyornithine/laminin, bovine collagen I, human extracellular extract, porcine skin gelatin or Matrigel. Cells can be passaged when they reach confluency, 80-90% confluency, or at any other level of confluency. Either aggregates of cells, single cell suspensions, or both, can be plated. To prepare cells for passaging, cells can be mechanically removed from adherent surfaces, for example by pipetting, or chemically removed by treatment with a protease such as trypsin-EDTA, collagenase or dispase.

All possible combinations of the first, second and third steps are contemplated. For example, in one procedure, the first step involves the use of serum-free medium without a growth factor, while the second and third steps involve the use of serum-free medium with a growth factor. In another procedure, all three steps involve the use of serum-free medium with a growth factor. In other procedures, the first and second steps are combined such that cells are exposed to the differentiation agent without a change in culture medium before being plated in the third step.

Effective concentrations of a differentiation agent can be determined by a dose-response analysis. The differentiation agent can be dissolved in a solvent such as dimethyl sulfoxide (DMSO), then added at various concentrations to ES cell cultures.

Any differentiation agent known to those of ordinary skill in the art is contemplated as a differentiation agent of the present invention. For example, for differentiation into neurogenic cell types such as dopaminergic cells, stromal derived induced activity (SDIA) may be employed, with co-culture on PA6 Feeder cells in appropriate medium. For late stage differentiation experiments, co cultures are enzymatically dissociated and re-plated on polyornithine-coated glass coverslips.

Cardiomyocytes are generated in suspension. ESC are dissociated at a single cell level, each cell generating floating structures in a defined medium called embryoid bodies.

After one week, the percentage of embryoid bodies containing beating cells (macroscopic evaluation) is quantified. In certain embodiments, Activin is included in the culture medium. In certain embodiments, the Activin used in the differentiation is Activin A, Activin B, Activin AB, or Activin C. In certain embodiments, more than one Activin may be used. In certain embodiments, other TGFβ superfamily members such as TGF-β, nodal, or lefty may be substituted instead of or in addition to the Activin in the methods of the present invention. In certain embodiments, the BMP used in the differentiation is BMP-2, BMP-4, or BMP-7. In certain embodiments, the BMP is a BMP other than BMP-2, BMP-4 or BMP-7 (excluding BMP-1). In certain embodiments, more than one BMP may be used.

The differentiating cells may be cultured in the absence of both Activin and BMP after the BMP step. An IGF may be included in that culture step. In certain of those embodiments, the IGF is included at a concentration between 10 ng/ml and 500 ng/ml; or between 25 ng/ml and 100 ng/ml; or between 50 ng/ml and 100 ng/ml. In certain embodiments, the IGF is included at concentrations less than 10 ng/ml or more than 500 ng/ml. The IGF may be IGF-1 or IGF-2. In certain embodiments, insulin may be substituted for the IGF in the methods of the present invention.

D. Selecting Cells

1. Characterization of Neural Precursor Cells, Neural Cells and Glial Cells

The extent of differentiation of ES cell cultures after exposure to different amounts of the differentiation agent can be determined by measuring the expression of promoters, genes and proteins active in neural precursor cells and/or neural cells. For example, expression of the Tα-1 promoter, the β3-tubulin gene and protein, the nestin gene and protein, the double-cortin gene and protein, the vimentin gene and protein, the NeuN gene and protein, or the MAP2 gene and protein can be analyzed. A typical range of concentrations for the dose-response analysis are 100 nM to 100 nM of the differentiation agent.

Differentiated cells prepared by exposure of undifferentiated stem cells to the differentiation agent can be characterized morphologically, immunochemically and in other ways to confirm their status as neural precursor cells.

Cells can be characterized according to a number of phenotypic criteria. The criteria include but are not limited to microscopic observation of morphological features, detection or quantitation of expressed cell markers, enzymatic activity, neurotransmitters and their receptors, and electrophysiological function.

Certain cells embodied in this invention have morphological features characteristic of neural cells or glial cells. These features are recognized by those of skill in the art. For example, neurons include small cell bodies, and multiple processes reminiscent of axons and dendrites.

Neural cells can also be characterized according to whether they express phenotypic markers characteristic of particular kinds of neural cells. Markers of interest include but are not limited to: a) β3-tubulin, microtubule-associated protein 2 (MAP-2), or neurofilament, characteristic of neurons; b) glial fibrillary acidic protein (GFAP), present in astrocytes; c) 2', 3'-cyclic nucleotide 3'-phosphodiesterase (CNPase) galactocerebroside (GalC) or myelin basic protein (MBP), characteristic of oligodendrocytes; d) Oct-4, characteristic of undifferentiated ES cells; e) Pax 6 and nestin, characteristic of neural precursors and other cells; f) Sox 1, characteristic of developing central nervous system; g) tyrosine hydroxylase (TH), present in catecholamine nuerons; h) glutamic acid decarboxylase, isoform 67 (GAD67), present in neurons containing gamma-aminobutyric acid; and i) vimentin, characteristic of intermediate neural differentiation.

Tissue-specific markers known in the art can be detected using any suitable immunological technique, such as flow immunocytochemistry and fluorescence activated cell sorting for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Antibody binding to an antigen can be observed by standard immunocytochemistry or flow cytometry assay, after fixation of the cells, using a labeled secondary antibody or other conjugate (such as a biotin-avidin conjugate) to amplify labeling, or other immunological methods well known in the art. In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference.

The expression of tissue-specific gene products can also be detected at the mRNA level by Northern blot analysis or dot-blot hybridization analysis, or by reverse transcriptase initiated polymerase chain reaction (RT-PCR) using sequence-specific primers in standard amplification methods which are described in detail in U.S. Pat. Nos. 4,683,195, 4,683,202 and 4,800,159, and in Innis et al., 1988, each of which is incorporated herein by reference in their entirety. Sequence data for the particular markers listed in this disclosure can be obtained from public databases, such as GenBANK. Expression of tissue-specific markers as detected at the protein or mRNA level is considered positive if the level is at least 2-fold, and preferably more than 10- or 50-fold above that of a control cell, such as an undifferentiated ES cell.

Also characteristic of neural cells, particularly terminally differentiated cells, are receptors and enzymes involved in the biosynthesis, release, and reuptake of neurotransmitters, and ion channels involved in the depolarization and repolarization events that relate to synaptic transmission. Evidence of synapse formation can be obtained by staining for synaptophysin. Evidence for receptivity to certain neurotransmitters can be obtained by detecting receptors for gamma amino butyric acid (GABA), glutamate, dopamine, 3,4-dihydroxyphenylalanine (DOPA), noradrenaline, acetylcholine, and serotonin.

Neural cells can be characterized according to a number of phenotypic criteria. The criteria include but are not limited to microscopic observation of morphological features, detection or quantitation of expressed cell markers, enzymatic activity, neurotransmitters and their receptors, and electrophysiological function.

Certain cells embodied in this invention have morphological features characteristic of neural cells or glial cells. These features are recognized by those of skill in the art. For example, neurons include small cell bodies, and multiple processes reminiscent of axons and dendrites.

Neural cells can also be characterized according to whether they express phenotypic markers characteristic of particular kinds of neural cells. Markers of interest include but are not limited to: a) β3-tubulin, microtubule-associated protein 2 (MAP-2), or neurofilament, characteristic of neurons; b) glial fibrillary acidic protein (GFAP), present in astrocytes; c) 2', 3'-cyclic nucleotide 3'-phosphodiesterase (CNPase) galactocerebroside (GalC) or myelin basic protein (MBP), characteristic of oligodendrocytes; d) Oct-4, characteristic of undifferentiated ES cells; e) Pax 6 and nestin, characteristic of neural precursors and other cells; f) Sox 1, characteristic of developing central nervous system; g) tyrosine hydroxylase (TH), present in catecholamine nuerons; h) glutamic acid decarboxylase, isoform 67 (GAD67), present in neurons containing gamma-aminobutyric acid; and i) vimentin, characteristic of intermediate neural differentiation.

Tissue-specific markers listed in this disclosure and known in the art can be detected using any suitable immunological technique, such as flow immunocytochemistry and fluorescence activated cell sorting for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Antibody binding to an antigen can be observed by standard immunocytochemistry or flow cytometry assay, after fixation of the cells, using a labeled secondary antibody or other conjugate (such as a biotin-avidin conjugate) to amplify labeling, or other immunological methods well known in the art. In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference.

The expression of tissue-specific gene products can also be detected at the mRNA level by Northern blot analysis or dot-blot hybridization analysis, or by reverse transcriptase initiated polymerase chain reaction (RT-PCR) using sequence-specific primers in standard amplification methods which are described in detail in U.S. Pat. Nos. 4,683,195, 4,683,202 and 4,800,159, and in Innis et al., 1988, each of which is incorporated herein by reference in their entirety. Sequence data for the particular markers listed in this disclosure can be obtained from public databases, such as GenBANK. Expression of tissue-specific markers as detected at the protein or mRNA level is considered positive if the level is at least 2-fold, and preferably more than 10- or 50-fold above that of a control cell, such as an undifferentiated ES cell.

Also characteristic of neural cells, particularly terminally differentiated cells, are receptors and enzymes involved in the biosynthesis, release, and reuptake of neurotransmitters, and ion channels involved in the depolarization and repolarization events that relate to synaptic transmission. Evidence of synapse formation can be obtained by staining for synaptophysin. Evidence for receptivity to certain neurotransmitters can be obtained by detecting receptors for gamma amino butyric acid (GABA), glutamate, dopamine, 3,4-dihydroxyphenylalanine (DOPA), noradrenaline, acetylcholine, and serotonin.

When evaluating neural differentiation using embryonic stem cells (ES), it is generally desirable to mimick as closely as possible physiological cellular interactions involved in neurogenesis. Methods involving air/liquid interface-based cultures of human ES are contemplated in the present methods. This culture system can allow for three-dimensional cell expansion and neural differentiation in the absence of added growth factors. In certain embodiments, culture methods such as those described in Eiraku et al. (2008), which is incorporated by reference in its entirety, may be used with the present invention.

2. Characterization of Cardiomyocytes

Any of the foregoing methods of characterization of cells for differentiation can be applied in assessing a cell for differentiation into a cardiomyocyte. Human embryonic stem cells may be co-cultured with mouse visceral endoderm (VE)-like cells to form beating muscle cells, expressing cardiac specific sarcomeric proteins and ion channels. This co-culture method permits induction of cardiomyocyte differentiation. Co-culture of pluripotent ES cells, including for example human ES cells, with END-2 cells induces extensive differentiation to two distinctive cell types from different lineages. One is epithelial and forms large cystic structures staining positively for alpha-fetoprotein and is presumably extraembryonic visceral endoderm; the others are grouped in areas of high local density and beat spontaneously. These beating cells are cardiomyocytes. Additional information concerning cardiomyocyte differentiation can be found in U.S. Patent App. Pub. Nos. 20080031857, 20080187494, and 20070010012, herein specifically incorporated by reference.

3. Characterization of Hepatocytes

Any of the foregoing methods of characterization of cells for differentiation can be applied in assessing a cell for differentiation into a hepatocyte. Methods for promoting differentiation of pluripotent stem cells into hepatocytes in vitro may involve removal of factors that prevent their differentiation and/or through the exposure to appropriate growth factors, for example as described in Sancho-Bru et al. (2009) or Zaret et al. (2008). iPS cells may be differentiated into hepatocytes and used for tissue replacement or gene therapy. Hepatic development may be initiated from iPSs by exposure to activin A. Further treatment with BMP-4 and bFGF can then differentiate cells towards a hepatic lineage (see, e.g., Zaret et al. (2008). Previous studies have indicated that human iPS cells have a hepatocyte-lineage differentiation potential comparable to that of ESCs (Si-Tayeb et al. (2010). Additional information concerning hepatocyte differentiation can be found in U.S. Patent App. Pub. Nos. 2010/0086525, 2010/0129351, 2005/0042750, 2010/0143313, 2010/0086999, WO 2010/049752A1, and U.S. Pat. No. 7,473,555 herein specifically incorporated by reference.

E. Screening Applications

The cells produced by the methods set forth herein can also be used to study the cellular and molecular biology of development, functional genomics, as well as the generation of differentiated cells for use in therapeutic or prophylactic transplantation, treatment, drug screening, or in vitro drug discovery. For example, the cells can be used for genomic analysis, to produce mRNA, cDNA, or genomic libraries, to produce specific polyclonal or monoclonal antibodies, including but not limited to humanized monoclonal antibodies (WO 01/51616, specifically incorporated herein by reference), or to screen for the effects of different test compounds or biologically active molecules on cells or tissues derived therefrom, such as pharmaceutical compounds in drug research. The cells can also be used to screen for factors (such as small molecule drugs, peptides, polynucleotides, and the like) or conditions (such as cell culture conditions or manipulations) that affect the characteristics of neural cells or cardiomyocytes in culture, and the differentiation of these cells.

The present invention includes methods for evaluating a test compound in neural cells or cardiomyocytes produced by the methods of the present invention. The test compound may be evaluated for whether it induces a change in phenotype or activity of the cells that results from the contact with the test compound. These assays may comprise testing a single test compound or random screening of large libraries of candidate substances; alternatively, the assays may be used to focus on particular classes of compounds selected with an eye towards structural attributes that are believed to make them more likely to modulate the function of neurons or neurally-committed cells. In certain embodiments, the toxicity of a test compound may be evaluated by contacting the compound with a plurality of neural or neurally-committed cells, such as cells which have formed into an engineered neural tissue (Schmandt et al., 2005) (e.g., derived from human embryonic stem-cells). ENTs are 3-dimensional pieces of tissues derived from embryonic stem cells (ES) which resemble certain layers of human fetal brain which may be produced via the differentiation of cells according to the present invention. The toxicity testing may be utilized as a part of an in vitro drug-screening process, e.g., prior to the clinical administration of the test compound to a subject, such as a human patient.

Various attributes may be evaluated to determine if a test compound results in toxicity in cells. Parameters including, for example, cell death (necrosis, apoptosis) excitotoxicity, cytotoxicity, altered neural function (e.g., altered generation of action potentials or long-term potentiation, etc.), altered brain receptor function, decreased resistance to challenge with a known toxic compound, synaptic toxicity, developmental neurotoxicity, or neural lineage—specific toxicity (e.g., in oligodendrocytes, astrocytes, or dopaminergic neurons) may be assessed in the cells to determine if a test compound results in toxicity or neurotoxicity. Electrophysiological techniques may be used to detect neural activity or function. Measure of synaptic markers may be used to detect compounds with a synaptic toxicity. Cells may be engineered to contain a promoter specific for a defined lineage (e.g., oligodendrocytes, dopaminergic neurons etc.) controlling the expression a reporter gene, such as a luminescent or fluorescent protein; in this way, neural lineage—specific toxicities may be more easily observed by changes in the expression of the reporter gene in vitro. In certain embodiments, reactive oxygen species may be measured to determine if a test compound results in increased cellular oxidative stress. In certain embodiments, dose-response relationships may be generated to assess the toxicity of a test compound. In certain embodiments, developmental neurotoxicity may be assessed by incubating a test compound cells during neural differentiation.

Multiple compounds or part or all of a small molecule library may be screened for toxicity or neural activity in cells cultured according to the present invention. Some or essentially all of the neural or neural-committed cells may be further differentiated into dopaminergic cells prior to the assessment of the toxicity of a test compound; this may be particularly useful in instances where it may be desirable to understand the dopaminergic toxicity of a compound.

The culturing and/or toxicity testing methods of the present invention may be automated. In certain embodiments, one or more of the steps involved with culturing cells, differentiating cells, and/or evaluating a property (e.g., the toxicity) of a test compound may be automated, e.g., via the use of robotics, to facilitate high-throughput toxicity assessment in cells. For example, various robotics may be used to culture cells, add or remove media from the cells, add a test compound to media comprising neural or neurally-committed cells differentiated according to the present invention. Specific robotics which may be used with the methods of the present invention include cell dispensers that allow automated and standardized distribution of cells in multiwells which typically range from 12 to 384 wells although a higher or lower number of wells can be used as desired (e.g., Matrix WellMate™ from Thermo Fisher Scientific, Inc.) and multichannel liquid handlers that allow automated distribution of library compounds into multiwell plates and automated dilutions of compounds, e.g., for $IC_{50}$ calculations (e.g., Zephyr from Caliper Life Sciences).

To assess the toxicity of a compound, one generally will determine the function and/or viability of cells in the presence and absence of the test compound. For example, a method generally comprises:

providing a test compound;

admixing the test compound with an isolated cell or plurality of cells produced according to the present invention;

measuring whether or not the candidate modulator can alter or disrupt cell viability or function in the cell or cells in step (c); and comparing the characteristic measured in step (c) with the characteristic of the cell or cells in the absence of said candidate modulator, wherein a difference between the measured characteristics indicates that said candidate modulator affects or exhibits toxicity against the cell or cells.

Screening may be carried out in a high-throughput assay using one or more multi-well plates, such as a 96 well plate. For example, ENTs may be produced in multi-well plates in order to establish a screening platform to study the neurotoxic potential of a test compound (e.g., a small molecule, protein, peptide, antibody, putative therapeutic) or multiple compounds (e.g., from a compound bank, small molecule library, peptide library, antibody library, etc.). Test compounds may be synthetically produced or purified from natural sources. Methods for producing ENTs and/or evaluating the properties of a test compound may be automated; for example, steps of adding or removing a compound or solution to a multi-well plate, detecting luminescence or fluorescence in a multi-well plate, and/or producing ENTs in a multi-well plate may be automated, e.g., via robotics.

In various embodiments, combinations of test compounds may be evaluated to determine if the simultaneous or sequential application of 2, 3, 4, 5, 6, or more test compounds to a neural cell, hepatocyte, or cardiomyocyte results in a particular effect or toxicity. The sequential administration of multiple compounds to a tissue may vary from seconds to hours, weeks, or longer, as desired. For example, in such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several weeks (1, 2, 3, 4, 5, 6, 7 or 8)

lapse between the respective administrations. Various combinations may be employed between test compound "A" and test compound"B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

In other embodiments, test compounds may be separately contacted with different neural, or neurally-committed tissue(s).

Specific neural promoters which may be used for this purpose include, for example, the Tα1 α-tubulin promoter (Tα1) and the βIII-tubulin promoter. Various promoters for specific neural lineages may be used to evaluate responses in specific cell types, including, e.g., dopaminergic neuron-specific promoters (e.g., tyrosine hydroxylase promoter), synapse-specific promoters (e.g., synapsin I promoter), axon-specific promoters (e.g., MAP2 promoter), and non-neural-specific promoters (e.g., oligodendrocytes assessed by CNPase II promoter). The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

In certain embodiments a pluripotent stem cell may be transfected with a dual reporter system to detect differentiation of the stem cell into a neural or neurally-committed cell. The dual reporter system may utilize a neuron-specific promoter to express a first luminescent or fluorescent protein and a second promoter (e.g., a promoter expressed by all cells or by a second cell type) can drive the expression of a second luminescent or fluorescent protein. In this way, the relative expression of neural markers may be observed. A reporter system may be transfected into a pluripotent cell via a variety of techniques including, e.g., liposomal transfection, microparticle bombardment, or viral transfection such as lentiviral transfection. In the below examples, a dual reporter system is used to observe expression of Firefly luciferase via the Tα1 promoter and Renilla luciferase via the EF1-α short promoter (EF1-αS).

Fluorescent proteins generally comprise a fluorescent chromophore, the chromophore being formed from at least 3 amino acids and typically characterized by a cyclization reaction creating a p-hydroxybenzylidene-imidazolidinone chromophore. The chromophore may not contain a prosthetic group and is capable of emitting light of selective energy, the energy having been stored in the chromophore by previous illumination from an outside light source comprising the correct wavelength(s). Spontaneously fluorescent proteins can vary widely in structure and the number of amino acids present in a chromophore, provided that the chromophore comprises the p-hydroxybenzylidene-imidazolidinone ring structure. In some instances, a fluorescent protein may comprise a β-barrel structure such as that found in green fluorescent proteins and described in Chalfie et al. (1994). Fluorescent proteins typically exhibit the ability to emit, in response to an incident light of a particular wavelength absorbed by the protein, a light of longer wavelength. Fluorescent activated cell sorting or (FACS) may be used to detect the expression of one or more neuron-specific markers in certain embodiments. FACS products are available, e.g., FACSCalibur™ (Becton Dickson) which may be used with the present invention.

Test compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other test compounds include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors. Peptidomimetics of peptide modulators or other compounds which are sterically similar to pharmacologically active compounds may also serve as test compounds.

It will, of course, be understood that all the screening methods of the present invention are useful in themselves notwithstanding the fact that toxicity or some other property may or may not be observed in or for a test compound.

F. Tissue Engineering and Cell Therapy

The present invention also contemplates the use of neural cells, hepatocytes, or cardiomyocytes produced by the methods of the present invention for cell-based therapies. The ability to regenerate human tissues that are substantially damaged due to disease or injury is reduced significantly in adults. The cells disclosed herein may be administered or transplanted into a mammalian subject for cell replacement therapy or tissue regeneration. Alternatively, the cells of the present invention may be directly administered to a subject. Therefore, the methods of the present disclosure may be useful in the treatment of many diseases, injuries, or other detrimental condition.

Cardiomyocytes, hepatocytes, or neural cells of the present invention can be used to modelize human body organs by 3-D tissue engineering. For example tissues in the human brain can be modelized by 3-D culturing of the neural cells produced by the methods set forth herein. Similarly, heart tissue may be derived and reconstructed from cardiomyocytes produced by the methods of the present invention. Liver tissue may be derived and reconstructed from hepatocytes produced by the methods of the present invention. The neural cells, hepatocytes, and cardiomyocytes of the present disclosure may also be used as carrier vehicles for various therapeutically active molecules or genes to be delivered at various sites of the human body, for example by genetically manipulating and differentiating the cells as required, and delivering the cells or tissue to a target site in a donor for gene therapy.

G. Treatment of Disease

In another aspect, the present invention provides a method of treating a disease in a subject that comprises administering to a subject with a disease an effective amount of neural cells or cardiomyocytes produced by the methods of the present invention. In some embodiments, dopaminergic neurons are administered to treat a nervous system disease or injury.

Neurodegenerative diseases and disorders for which the invention may be effective include, but are not limited to: Alzheimer disease, Parkinson's disease, multiple sclerosis, stroke, amyotrophic lateral sclerosis (Lou Gehrig's Disease), frontotemporal dementia (Pick's Disease, prion disease, Huntington's disease, cerebral ischemia, idiopathic Morbus Parkinson, topically- or drug-induced Parkinson syndrome, Morbus Alzheimer and cerebral dementia syndromes of different origin, Huntington's chorea, infectious-induced neurodegeneration disorders such as AIDS-encephalopathy, Creutzfeld-Jakob disease, encephalopathies induced by rubiola and herpes viruses and borrelioses, metabolic-toxic neurodegenerative disorders such as hepatic-, alcoholic-, hypoxic-, hypo- or hyperglycemically-induced encephalopathies as well as encephalopathies induced by solvents or pharmaceuticals, degenerative retina disorders of various origin, traumatically-induced brain and bone marrow damage, spinal cord injuries, cerebral hyperexcitability symptoms of varying origin such as after the addition of and/or withdrawal of medicaments, toxins, noxae and drugs, mentally and traumatically-induced cerebral hyperexcitability states, neurodegenerative syndromes of the peripheral nervous system, such as metabolism, medicament, toxically- and infectiously-induced polyneuropathies and polyneuritis, and the bronchospasmolytic effect.

Liver diseases and disorders for which the invention may be effective include, but are not limited to: hepatitis, non-alcoholic fatty liver disease, cirrhosis, cancer of the liver, Wilson's disease, primary sclerosing cholangitis, primary biliary cirrhosis, autoimmune disease of small bile ducts, Budd-Chiari syndrome, Gilbert's syndrome, glycogen storage disease type II, acute liver failure, Alagille syndrome, alpha-1 antitrypsin deficiency, autoimmune hepatitis, biliary atresia, glycogen storage disease, hepatoblastoma, hepatocellular carcinoma (hepatoma), progressive familial intrahepatic cholestasis (PFIC), and urea cycle disorder.

1. Pharmaceutical Formulations

The neural cells, hepatocytes, or cardiomyocytes produced by the methods of the present invention may be included in a pharmaceutical composition. Pharmaceutical compositions of the cells can be administered by any method known to those of ordinary skill in the art. For example, administration may be by direct injection into damaged areas of the nervous system, or administered parenterally, intravenously, intradermally, intramuscularly, transdermally, intraperitoneally, or intrathecally.

For injection, solutions of cells in aqueous media. The pharmaceutical forms suitable for injectable use include sterile aqueous solutions. The carrier can be a solvent or dispersion medium containing, for example, water, ethanol, polyol (e.g., glycerol, propylene glycol, and liquid polyethylene glycol, and the like), suitable mixtures thereof, and/or vegetable oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. The person responsible for administration will, in any event, determine the appropriate dose for the individual subject.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

2. Administration

For treatment of nervous system damage, a subject is administered a pharmaceutically effective amount of cells of the present invention. The routes of administration will vary, naturally, with the location and nature of the damage, and include, e.g., intradermal, intrathecal, injection into the central nervous system, intracardiac, transdermal, parenteral, intravenous, intramuscular, intranasal, subcutaneous, percutaneous, intratracheal, intraperitoneal, perfusion, lavage, and direct injection.

The cells can be given in a single dose, or multiple doses. Continuous administration also may be applied where appropriate. Generally, the dose of a therapeutic composition via continuous perfusion will be equivalent to that given by a single or multiple injections, adjusted over a period of time during which the perfusion occurs. The dose of cells administered will be dependent on the subject being treated, the subject's weight, the manner of administration, and the judgment of the physician. Treatment regimens may vary as well, and often depend on the type of nervous system damage, location of the damage, disease progression, and health and age of the patient.

3. Combination Treatments

In certain embodiments, the compositions and methods of the present invention involve the administration of clonal cells produced by the methods of the present invention and one or more additional therapies. Such therapy can be applied in the treatment of any disease for which treatment with the clonal cells of the present invention are contemplated. For example, the disease may be a neurodegenerative disease, a cardiovascular disease, a liver disease, or a hyperproliferative disease such as cancer.

The methods and compositions including combination therapies enhance the therapeutic or protective effect, and/or increase the therapeutic effect of another therapy. Therapeutic and prophylactic methods and compositions can be provided in a combined amount effective to achieve the desired effect, such as the treatment of neurodegeneration or treatment of cardiovascular disease.

Clonal cells of the present invention may be administered before, during, after or in various combinations relative to a secondary form of therapy. The administrations may be in intervals ranging from concurrently to minutes to days to weeks. One would generally ensure that a significant period of time did not expire between the time of each delivery, such that the two compounds would still be able to exert an advantageously combined effect on the patient. The cells and secondary therapy may be administered within about 12 to 24 or 72 h of each other and, more preferably, within about 6-12 h of each other. In some situations it may be desirable to extend the time period for treatment significantly where several days (2, 3, 4, 5, 6 or 7) to several weeks (1, 2, 3, 4, 5, 6, 7 or 8) lapse between respective administrations.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24-hour period), the patient may be given one or multiple administrations of the cells(s). Moreover, after a course of treatment, it is contemplated that there is a period of time at which no treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Various combinations may be employed. For the example below clonal cells of the present invention are represented as "A" and a secondary form of therapy is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy. It is expected that the treatment cycles would be repeated as necessary. It also is contemplated that various standard therapies, as well as surgical intervention, may be applied in combination with the described therapy.

In various embodiments, cells derived by methods of the present invention (e.g., cardiomyocytes, hepatocytes, neural cells, dopaminergic neurons, etc.) may be administered to a patient in combination with an immunosuppressant. In other embodiments, it may be unnecessary to administer an immunosuppressant in combination with cells of the present invention. For example, an iPS cells may be produced from cells from a subject and subsequently re-differentiated into a desired cell type; these cells may then be therapeutically administered back into the subject. The re-differentiated cells may result in little or no adverse immunological response, since the cells were derived from cells of the subject. Nonetheless, in various embodiments, an immune suppressant or anti-inflammatory compound may be advantageously administered to the patient if, e.g., the patient has an inflammatory or autoimmune disease.

In specific aspects, it is contemplated that a standard secondary therapy may include pharmacotherapy, chemotherapy, immunotherapy, surgical therapy, radiotherapy, or gene therapy and may be employed in combination with the clonal cells described herein. Below are non-limiting examples of secondary forms of pharmacotherapy:

a. Cardiovascular Drugs

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof.

In addition, it should be noted that any of the following may be used to develop new sets of cardiac therapy target genes as β-blockers were used in the present examples (see below). While it is expected that many of these genes may overlap, new gene targets likely can be developed.

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of athersclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

Non-limiting examples of resins/bile acid sequesterants include cholestyramine (cholybar, questran), colestipol (colestid) and polidexide.

Non-limiting examples of HMG CoA reductase inhibitors include lovastatin (mevacor), pravastatin (pravochol) or simvastatin (zocor).

Non-limiting examples of nicotinic acid derivatives include nicotinate, acepimox, niceritrol, nicoclonate, nicomol and oxiniacic acid.

Non-limiting examples of thyroid hormones and analogs thereof include etoroxate, thyropropic acid and thyroxine.

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5, 8, 11, 14, 17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

Non-limiting examples of an antiarteriosclerotic include pyridinol carbamate.

In certain embodiments, administration of an agent that aids in the removal or prevention of blood clots may be combined with administration of a modulator, particularly in treatment of athersclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

Non-limiting examples of antiplatelet agents include aspirin, a dextran, dipyridamole (persantin), heparin, sulfinpyranone (anturane) and ticlopidine (ticlid).

Non-limiting examples of thrombolytic agents include tissue plaminogen activator (activase), plasmin, pro-urokinase, urokinase (abbokinase) streptokinase (streptase), anistreplase/AP SAC (eminase).

In certain embodiments wherein a patient is suffering from a hemmorage or an increased likelihood of hemorrhaging, an agent that may enhance blood coagulation may be used. Non-limiting examples of a blood coagulation promoting agent include thrombolytic agent antagonists and anticoagulant antagonists.

Non-limiting examples of anticoagulant antagonists include protamine and vitamine K1.

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

Non-limiting examples of antiarrhythmic agents include Class I antiarrythmic agents (sodium channel blockers), Class II antiarrythmic agents (beta-adrenergic blockers), Class II antiarrythmic agents (repolarization prolonging drugs), Class IV antiarrhythmic agents (calcium channel blockers) and miscellaneous antiarrythmic agents.

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocaine), tocainide (tonocard) and mexiletine (mexitil). Non-limiting examples of Class IC antiarrhythmic agents include encainide (enkaid) and flecainide (tambocor).

Non-limiting examples of a beta blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

Non-limiting examples of an agent that prolong repolarization, also known as a Class III antiarrhythmic agent, include amiodarone (cordarone) and sotalol (betapace).

Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexiline. In certain embodiments a calcium channel blocker comprises a long-acting dihydropyridine (nifedipine-type) calcium antagonist.

Non-limiting examples of miscellaneous antiarrhymic agents include adenosine (adenocard), digoxin (lanoxin), acecainide, ajmaline, amoproxan, aprindine, bretylium tosylate, bunaftine, butobendine, capobenic acid, cifenline, disopyranide, hydroquinidine, indecainide, ipatropium bromide, lidocaine, lorajmine, lorcainide, meobentine, moricizine, pirmenol, prajmaline, propafenone, pyrinoline, quinidine polygalacturonate, quinidine sulfate and viquidil.

Non-limiting examples of antihypertensive agents include sympatholytic, alpha/beta blockers, alpha blockers, antiangiotensin II agents, beta blockers, calcium channel blockers, vasodilators and miscellaneous antihypertensives.

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

In certain embodiments, an antihypertensive agent is both an alpha and beta adrenergic antagonist. Non-limiting examples of an alpha/beta blocker comprise labetalol (normodyne, trandate).

Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan.

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting examples of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexiline, pimefylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative.

Non-limiting examples of arylethanolamine derivatives include amosulalol, bufuralol, dilevalol, labetalol, pronethalol, sotalol and sulfinalol.

Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide; epithiazide, ethiazide, fenquizone, hydrochlorothizide, hydroflumethiazide, methyclothiazide, meticrane, metolazone, paraflutizide, polythizide, tetrachlormethiazide and trichlormethiazide.

Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Non-limiting examples of dihydropyridine derivatives include amlodipine, felodipine, isradipine, nicardipine, nifedipine, nilvadipine, nisoldipine and nitrendipine.

Non-limiting examples of guanidine derivatives include bethanidine, debrisoquin, guanabenz, guanacline, guanadrel, guanazodine, guanethidine, guanfacine, guanochlor, guanoxabenz and guanoxan.

Non-limiting examples of hydrazines/phthalazines include budralazine, cadralazine, dihydralazine, endralazine, hydracarbazine, hydralazine, pheniprazine, pildralazine and todralazine.

Non-limiting examples of imidazole derivatives include clonidine, lofexidine, phentolamine, tiamenidine and tolonidine.

Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Non-limiting examples of reserpine derivatives include bietaserpine, deserpidine, rescinnamine, reserpine and syrosingopine.

Non-limiting examples of sulfonamide derivatives include ambuside, clopamide, furosemide, indapamide, quinethazone, tripamide and xipamide.

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

Non-limiting examples of agents for the treatment of congestive heart failure include anti-angiotension II agents, afterload-preload reduction treatment, diuretics and inotropic agents.

In certain embodiments, an animal patient that cannot tolerate an angiotension antagonist may be treated with a combination therapy. Such therapy may combine administration of hydralazine (apresoline) and isosorbide dinitrate (isordil, sorbitrate).

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furterene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexiline, ticrnafen and urea.

Non-limiting examples of a positive inotropic agent, also known as a cardiotonic, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include amrinone (inocor).

Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

Surgical therapies are contemplated as secondary therapies. Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support, heart transplant, angioplasty, valve replacement surgery, coronary artery bypass grafting, or a combination thereof. Non-limiting examples of a mechanical circulatory support that may be used in the present invention comprise an intra-aortic balloon counterpulsation, left ventricular assist device or combination thereof.

b. Secondary Therapies of Neurodegenerative Disease

Examples of secondary therapy of neurodegenerative disease include medical therapies or surgical therapies. Non-limiting examples of medical therapies include cholinesterase inhibitors. Examples include donezepil, rivastigmine, galantamine. Other examples of secondary therapies include agents that regulate glutamate in the brain, such as Memantine. Further examples include antioxidants such as vitamin E. Antipsychotic agents, neuroleptics, antidepressants, anxiolytics, and sleep aids are also contemplated as secondary forms of therapy. Other secondary agents include selegiline, a selective monoamine oxidase inhibitor, an estrogen, anti-inflammatory drugs, and *Ginkgo biloba.*

Secondary therapies also include levodopa, dopamine agonists, and COMT inhibitors.

Secondary surgical therapies include ablation, deep brain stimulation, pallidotomy, and cerebral transplantation of dopamine-producing cells other than cells of the present invention.

c. Secondary Therapies of Liver Disease

Examples of secondary therapy of liver disease include medical therapies or surgical therapies. Non-limiting examples of medical therapies include sulfasalazine, a corticosteroid, an anti-inflammatory compound, a cytokine-directed therapy (e.g., pentoxifylline or anti-TNF, an antioxidant, and anti-viral therapies.

d. Chemotherapeutic Agents

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas. Examples of these agents have been previously set forth.

H. Kits

In various aspects of the invention, a kit is envisioned containing one or more sealed containers that include a clonal population of cells of the present invention. In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass.

The kit may further include an instruction sheet that outlines procedural steps concerning methods of the present invention or information concerning the clonal population of cells such as source, storage instructions, administration instructions, etc. The instruction information may be in a computer readable media containing machine-readable instructions that, when executed using a computer, cause the display of a real or virtual procedure of delivering a pharmaceutically effective amount of a therapeutic agent. The kit may optionally include one or more additional therapeutic agents that can be applied in the treatment or prevention of a disease. For example, the additional therapeutic agent may be an agent that can be applied in the treatment or prevention of a neurodegenerative disease or a cardiovascular disease. Non-limiting examples of such agents are discussed elsewhere in this specification.

I. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell culture: The mouse CGR8 ESC line was obtained from the European Collection of Cell Culture (ATCC); the stromal PA6 cell line was provided by the Riken BRC cell bank, Japan. The CGR8 embryonic stem cell lines were maintained in BHK-21 medium supplemented with 10% fetal calf serum, 2 mM L-glutamine, 1% non-essential amino acids, 1 mM sodium pyruvate, 1% penicillin/treptomycin (Gibco, Invitrogen, Grand Island, N.Y., USA; world wide web at invitrogen.com), and leukemia inhibitory factor. CGR8 were cultured on gelatin-coated dishes. PA6 stromal cell line was maintained in MEM-alpha medium supplemented with 10% fetal bovine serum (Gibco, Invitrogen).

Antibodies: The following primary antibodies were used: mouse anti-nestin, mouse anti-neuronal nuclei-specific protein (NeuN), rabbit anti-tyrosine hydroxylase, rat anti-dopamine transporter (DAT) (Chemicon, Temecula, Calif., USA; world wide web at chemicon.com), mouse anti-tyrosine hydroxylase (Santa Cruz Biotechnology Inc., Santa Cruz, Calif., USA; world wide web at scbt.com), mouse anti-beta-III-tubulin (Sigma-Aldrich, St. Louis, Mo., USA; world wide web at sigmaaldrich.com), and rabbit anti-beta-III-tubulin (Covance, Princeton, N.J., USA; world wide web at covance.com). The following fluorochrome-labeled secondary antibodies were used: Alexa Fluor (555 or 488)-labelled antibodies from goat or donkey against mouse, goat, or rabbit (Molecular Probes, Eugene, Oreg., USA; probes.invitrogen.com); Cy5-conjugated donkey against mouse IgG, PE-Cy5.5 goat against rabbit IgG (Jackson Immunoresearch Laboratories, USA; world wide web at jacksonimmuno.com).

Flow cytometry: Cells were labelled with 1.25 µmol/L 5,6-carboxy-fluorescein-succinimidyl-ester (CFSE, Sigma) according to the manufacturer's recommendations. The following antibodies used were against nestin and beta-III-tubulin. For their intracellular detection, cells were fixed with paraformaldehyde 0.5% for 10 min at room temperature under constant stirring before incubation (45 min) with appropriate dilutions of antibodies in PBS containing 0.2% Triton X-100 and 10% foetal bovine serum. Cells were rinsed twice with PBS, incubated for 45 min with appropriate secondary antibodies, and washed before fluorescent active cell sorting (FACS) analysis. Fluorescence was analyzed with a FACSCalibur flow cytometer (Becton Dickinson, Franklin Lakes, N.J., USA; world wide web at bd.com) and the CellQuest software.

Immunofluorescence and microscopy: Glass coverslips containing cells were fixed with 2% paraformaldehyde in PBS for 15 min at room temperature before permeabilization with Triton X-100 0.2% in PBS for an additional 30 min. After washing with PBS, coverslips were incubated overnight at +4° C. with appropriate dilutions of primary antibodies in PBS containing 1% of fetal bovine serum. After washing in PBS, coverslips were incubated for 1 h at room temperature with the appropriate dilution of secondary antibodies, washed again, and incubated for 15 min with 300 nM 4,6-diamidino-2-phenylindole (DAPI). Cells were washed in PBS and rinsed with water before inclusion in FluorSave mounting medium (Calbiochem, San Diego, Calif.; USA; world wide web at emdbiosciences.com). Automated imaging was performed with the imageXpress automated fluorescence microscope using the MetaXpress software (Molecular Devices).

Neural differentiation of ESC: ESCs were washed with PBS before plating at low density (100 cell/cm$^2$) on a confluent layer of irradiated (5000 rad) PA6. The medium for differentiation comprised: GMEM, 15% knockout serum replacement, 2 mM L-glutamine, 1 mM sodium pyruvate, 1 mM non-essential amino acids, 0.1 mM beta-mercaptoethanol, 1% penicillin/streptomycin (Gibco, Invitrogen). In some experiments, cells ongoing neural dissociation were dissociated using trypsin/EDTA 0.5% and re-plated on poly-ornithine-coated cell culture Petri dishes (0.001%) at the density of 5000 cells/cm$^2$.

Generation of embryoid bodies: CGR8 was washed once with PBS and dissociated using trypsin/EDTA 5%. Cells were diluted in culture medium without leukemia inhibitory factor and put on 20 µl drops of 500 cells on the cover of cell plates. Two days later, cells forming embryoid bodies were pooled in 10 ml ultralow attachment plates and left once again for three days in the incubator. On the day 5, embryoid bodies were plated on gelatin-coated dishes. First embryoid bodies started beating on day 7. Culture medium was changed every two days.

Lentivectors and ESC transduction: To generate entry vectors, the promoters (eta-IIIp and Talpha-1) and genes of interest (GFP and H2B-mRFP1) were cloned into pDONRP4-P1R and pDONR221, respectively, using the Gateway® BP clonase enzyme mix (Invitrogen). The resulting entry vectors were then recombined into 2K7$_{bsd}$ or 2K7$_{neo}$ lentivectors using the Gateway® LR plus clonase enzyme mix (Invitrogen). The lentivector particles were produced by transient transfection in 293T cells using calcium phosphate. The lentivector-containing supernatant was collected after 72 h, filtered through 0.45-µm pore-sized polyethersulfone membrane and concentrated 120-fold by ultracentrifugation (50,000×g, for 90 min. at 4° C.). The pellet was re-suspended in ESC culture medium and subsequently added to the target cells. Three days after transduction, blasticidin (7.5 µg/ml) or neomycin (400 µg/ml) was added to the culture medium and the selection was maintained for six (blasticidin) or 10 days (neomycin).

Microarrays: Total RNA was isolated with the RNA mini Kit (Quiagen, city, country) and quality controlled for RNA integrity by capillary electrophoresis on Agilent 2100 Bioanalyzer (Agilent Technologies, Palo Alto, Calif., USA). 500 ng was amplified and labelled using the Illumina TotalPrep RNA Amplification kit (Ambion, city, country). cRNA quality was assessed by capillary electrophoresis on Agilent 2100 Bioanalyzer. Hybridization on human expression arrays (Illumina, city, country) was carried out according to the manufacturer's instructions.

Data were normalized and analyzed using Illumina Beadstudio 3.1.3 (background correction and quantile normalization). Expression profiles of each sample were imported into GeneSpringGX 7.3.1 (Agilent Technologies). In addition to expression values, Illumina BeadStudio software computes a detection p-value. Based on this, each probe was assigned a detection flag (P (present): p<0.045; M (marginal): p between 0.050 and 0.045, A (absent): p>0.05). To identify differentially expressed transcripts, Student's t-test and/or ANOVA and additional steps of filtering were carried out. Enrichment analysis for functional ontologies was made using MetaCore software (world wide web at genego.com).

Cytogenetic and molecular analysis: ESC were treated with colcemid (Invitrogen) at 50 ng/ml for 4 h. Mitotically-arrested cells were subjected to hypotonic treatment using KCl 0.075 M for 5 min, fixed by changing the solution with Carnoy's fixative (methanol:acetic acid=3:1, v/v) 3 times, after which the solution containing the cells was spread on a glass slide. Chromosomes were subsequently G-banded according to the standard procedure. Oligonucleotide array-comparative genomic hybridization (Array-CGH) analyses were performed according to the manufacturer's protocol using the Mouse Genome CGH Microarray Kit 244B (Agilent Technologies) covering the whole genome with a resolution of ~20 kb. Data were analyzed with Agilent CGH analytics 3.4 software, using the statistical algorithms z-score and ADAM-2 according to sensitivity threshold respectively at 2.5 and 6.0 and a moving average window of 0.2 Mb. Mapping data were analyzed on the mouse genome sequence using the NCBI database Build 37 (world wide web at ncbi.nlm.nih.gov).

Example 2

Cellular Diversity within Embryonic Stem Cells: Pluripotent Clonal Sublines Show Distinct Differentiation Potential Embryonic stem cells (ESCs), derived from the early inner cell mass (ICM), are constituted of theoretically homogeneous pluripotent cells. This study was designed to test this concept, using experimental conditions that allowed characterization of progenies derived from one parental ESC. Flow cytometry and live imaging analyses demonstrated that some individual ESC submitted to neural differentiation generate progenies that escape early to the desired phenotype. It was not due to a delayed differentiation program but to significant variations in the capacity of individual parental ESC to generate neurons, thus raising the possibility of a clonal diversity among ESC. To further substantiate this hypothesis, clonal sublines from mouse ESC were generated by a limit dilution method. Transcriptome analysis of these clonal lines showed marked differences in gene expression profile despite the fact that all clones expressed comparable levels of pluripotency markers (including Oct4, Nanog, Sox2, Klf4). The different clones showed distinct differentiation potential, both in phenotypic differentiation assays and with respect to gene expression in embryoid bodies. To demonstrate the wider applicability of these findings, clones were generated from another ESC line. These clonal sublines also showed marked individualities in their differentiation potential. Taken together these observations demonstrate that pluripotent ESCs consist of individual cell types with distinct differentiation potentials. These findings not only identify novel elements for the biological understanding of ESC, but also provide new tools with a major potential for their future in vitro and in vivo use.

Differentiation of ESC Generates Proliferating Cells that Escape Early to the Neural Fate.

During differentiation of ESC, typically a fraction of cells do not acquire the desired cellular phenotype. Although this may be due to anisochronicity, i.e., a delay of a subpopulation to progress in the maturation process, a subpopulation of cells might escape the desired differentiation because of inherent resistance to the differentiation protocol. To address this question, the inventors developed a flow cytometry assay combining immunodetection of differentiation markers with an analysis of cell division.

Mouse CGR8 ESC were cultured for 5 days at low density on a confluent layer of irradiated stromal cells (PA6) (Shintani et al., 2008) to induce early differentiation and, when indicated, dissociated and plated on polyornithin to progress towards more advanced neural differentiation. Undifferentiated ESC were negative for nestin and beta-III-tubulin (FIG. 1A, left panel). At day 5 of differentiation, a complex pattern of cellular expression of the two markers was observed (FIG. 1A, right panel) with beta-III-tubulin-positive, nestin-negative neuronal cells, nestin-positive beta-III-tubulin-negative precursor cells, and a small population of double-positive transition cells. Of note, a sizeable population of double-negative cells was observed, but these were not due to a delayed exit of a subpopulation from the pluripotency state as S SEA-1 expression was abolished after 5 days of differentiation in both nestin-positive and -negative populations (FIG. 1B).

The synchronicity of cell division was also monitored using the fluorescent probe carboxy-fluorescein-succinimidyl-ester (CFSE) (Lyons, 2000). CFSE is a stable and non-toxic fluorescent dye diluted by 50% in daughter cells after each cell division and thereby allows flow cytometry quantification of the number of mitotic events. A non-dividing cell maintains the initial level of CFSE fluorescence, while dividing cells lose fluorescence as a function of the number of divisions. As shown in the monophasic CFSE histograms, most cells divided during early neural differentiation (FIG. 1C, left panel). In contrast, the multiphasic CFSE histograms show that a subpopulation of cells slows down or stops division during late neural differentiation (FIG. 1C, right panel).

Cell proliferation was then analyzed as a function of cellular differentiation markers during late neural differentiation at 24 h, 48 h, and 72 h after plating on polyornithin (FIG. 1D). Two days after plating, the neuronal subpopulation (nestin-negative/beta-III-tubulin-positive) slowed down its proliferation (higher CFSE intensity) in comparison to neuroepithelial (nestin-positive/beta-III-tubulin-negative) and non-neural cells (nestin-negative/beta-III-tubulin-negative) that actively proliferated (lower CFSE intensity). Three days after re-plating, the neuronal population included cells that had definitively stopped division, whereas non-neural and neuroepithelial cells continued division. Of note, several peaks corresponding to different CFSE intensities were observed within the three subpopulations, demonstrating also heterogeneity among them.

Taken together, these observations show that all ESC started a differentiation program, but some cells escaped to the neural fate at a very early stage and generated mixed cultures where post-mitotic neurons coexist with proliferating neural progenitors and non-neural cells. This escape response could be explained by a heterogeneity among ESC submitted to neural differentiation.

Individual ESCs Submitted to Neural Differentiation Generate a Defined Progeny.

Figure 2:
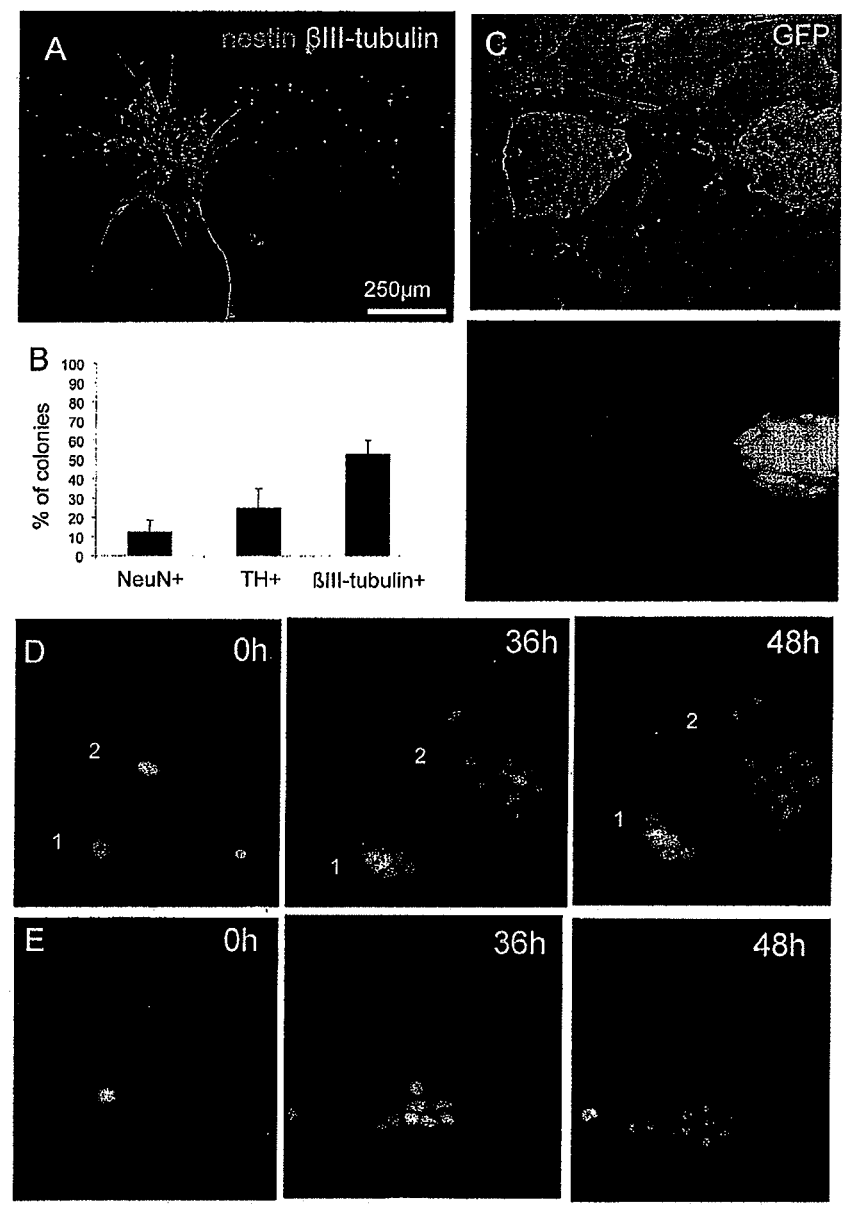
FIGS. 2A-E. Variability of progenies derived from individual parental ESC.

The hypothesis of heterogeneity among ESC was then investigated. Experimental conditions were designed that allowed for characterization of progenies derived exclusively from one individual ESC. Neural differentiation was induced by plating ESC at very low density on PA6 stromal cells. Under these conditions, single ESC generate a colony with ongoing differentiation and the nature of each progeny can be monitored. After three days, ESC-derived colonies were heterogeneous. Some colonies included cells with a neural phenotype (nestin+ and βIII-tubulin+) whereas other colonies were non-neural (double-negative) (FIG. 2A). This observation indicated strong variations in the nature of the progeny derived from one single ESC. Quantification showed that half of the colonies included βIII-tubulin+ neuronal cells after three days (FIG. 2B). At a later stage of differentiation, 25% of colonies included neurons with a dopaminergic phenotype (tyrosine hydroxylase-positive (TH)+), and 10% of colonies included mature-stage neurons (NeuN+) (FIG. 2B). Heterogeneity between colonies was confirmed using two other neural progenitor cells markers, Pax-6 and Sox-1. Heterogeneity between colonies for neural commitment was confirmed using a genetically-modified ESC line expressing the green fluorescent protein (GFP) under the control of the early neural-specific promoter Tα1 (Suter et al., 2009). In accordance with the previous observation, ESC-Tα1-GFP submitted to neural differentiation induced GFP+ and GFP− colonies (FIG. 2C), confirming the coexistence of neural and non-neural progenies. Thus, the capacity of some cells to escape to the neural fate is linked to the nature of the parental cell from which they derive.

Figure 7:
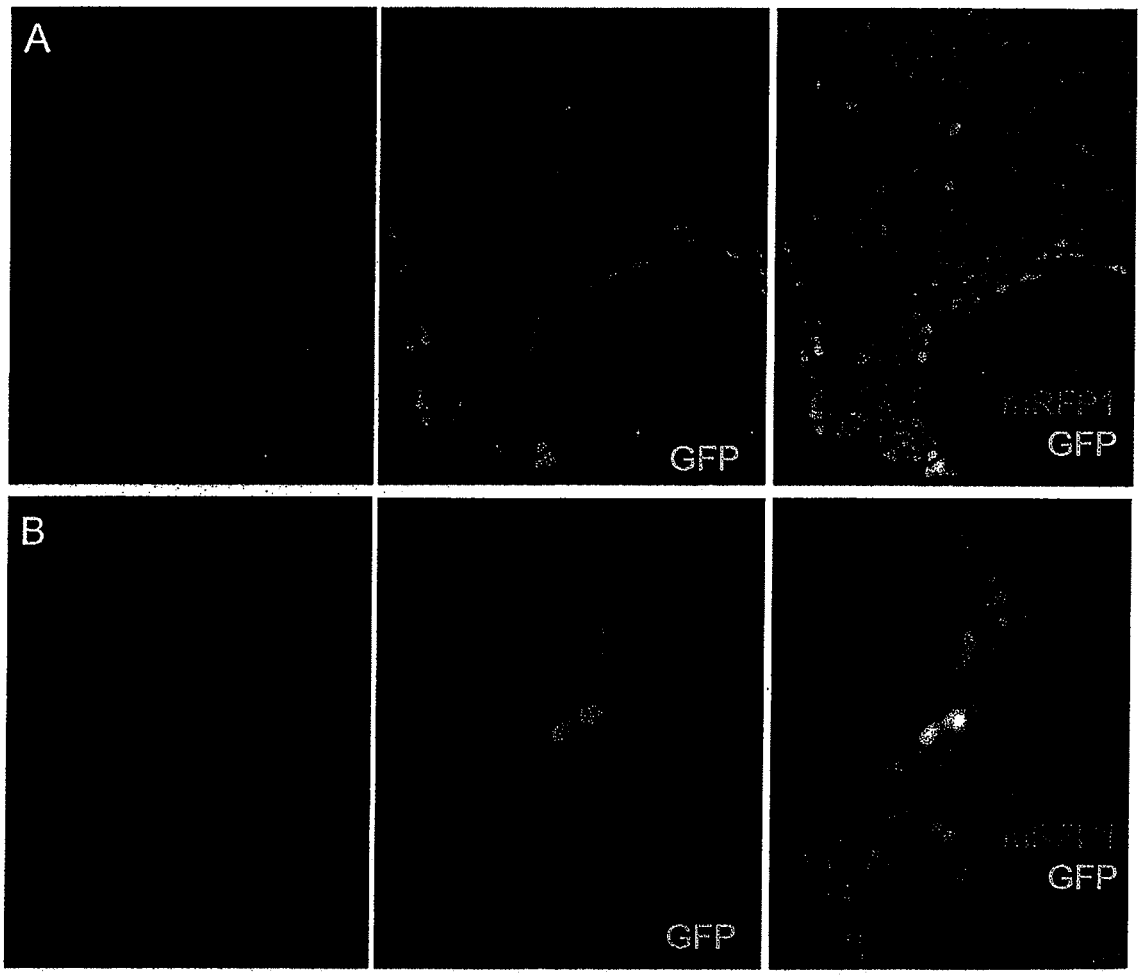
FIGS. 7A-B. Specificity of the beta-III-tubulin promoter.

The observed variability between the different progenies was analyzed in greater detail using a promoter/reporter gene-based method. A genetically-modified CGR8 ESC line was developed to express the GFP under the control of the βIII-tubulin promoter (βIIIp). These ESC-βIIIp-GFP cells were co-transduced with a lentivector expressing the monomeric red fluorescent protein (mRFP1) fused to the H2B histone for its targeting to cell nuclei. This allowed ESC-βIIIp-GFP-H2B-mRFP1 to be visualized by fluorescence microscopy because of their red fluorescent nuclei. The promoter for βIII-tubulin is constitutively active at a low level in undifferentiated ESC. In contrast, GFP expression is decreased in nestin-non neural populations (FIG. 7A), whereas a higher GFP expression is induced in βIII-tubulin+ neuronal cells (FIG. 7B). ESC-βIIIp-GFP-H2B-mRFP1 were plated on PA6 for neural differentiation and several individual ESC were followed during two days using an automated high throughput imaging system (ImageXpress, Molecular Devices). Imaging confirmed that undifferentiated ESC-βIIIp-GFP-H2B-mRFP1 express a background level of GFP and divide rapidly after plating. In some colonies, GFP expression was maintained or increased in the ESC-derived progeny (FIG. 2D, colony 1). In other colonies, the GFP expression was rapidly abolished in all cells (FIG. 2D, colony 2), confirming that some individual ESCs generate a non-neural progeny. Finally, colonies where only a fraction of cells switched off GFP expression were also observed (FIG. 2E) and indicated that the progeny derived from one individual ESC could be also a mix between neural and non-neural cells.

Figure 8:
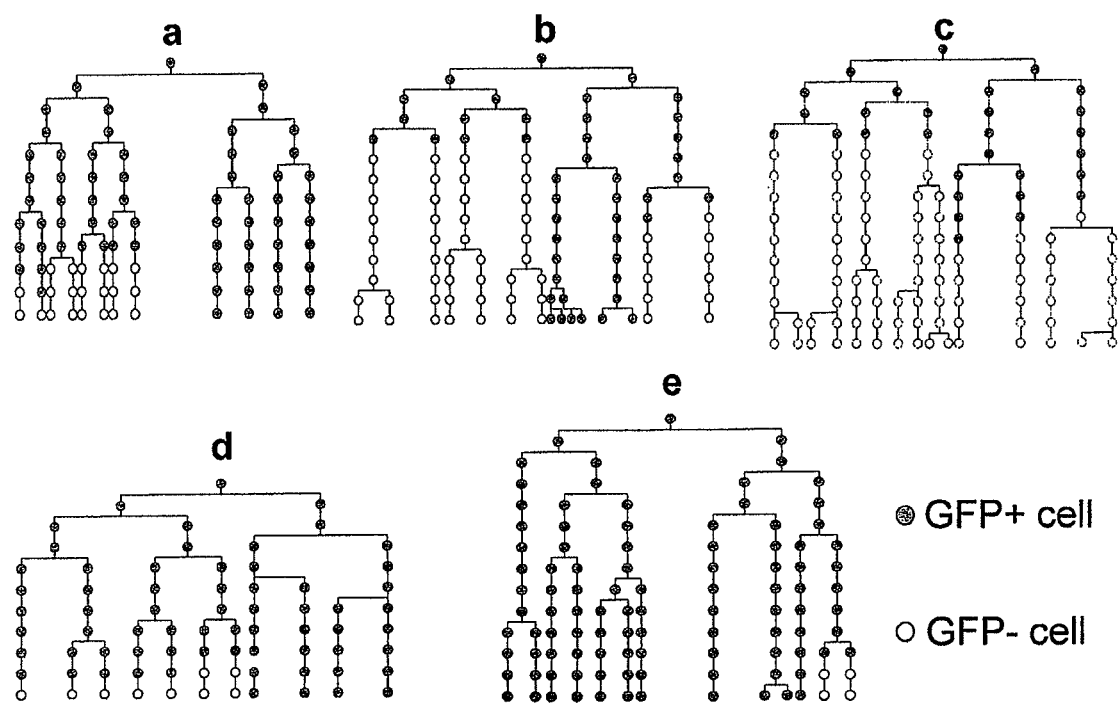
FIG. 8. Phylogeny of the progeny derived from individual parental ESC. Phylogenic trees were established from the imaging described in FIG. 2. Five examples of phylogenic trees are presented.

Phylogenic trees including GFP expression were established from live imaging movies. None of all the analyzed phylogenic trees was identical, thus confirming the uniqueness of progenies derived from individual ESCs. For example, it can be observed that a part (FIGS. 8 A, B, D) or the totality (FIG. 8C) of the progeny switched off GFP expression. In other colonies, the promoter remained active in most cells after two days (FIG. 8D). Interestingly, cells that have switched off GFP expression were frequently derived exclusively from one of the two daughter cells generated by the first division. In contrast, those which kept GFP expression were derived from the other daughter cell, indicating that the first division produced two different daughter cells that generate respectively different progenies.

Taken together, these observations confirm that individual ESCs generate defined progenies and do not share the same potential for the generation of neural progenies.

Clonal Diversity Among ESC Corresponding to the Early Pluripotent ICM.

Figure 3:
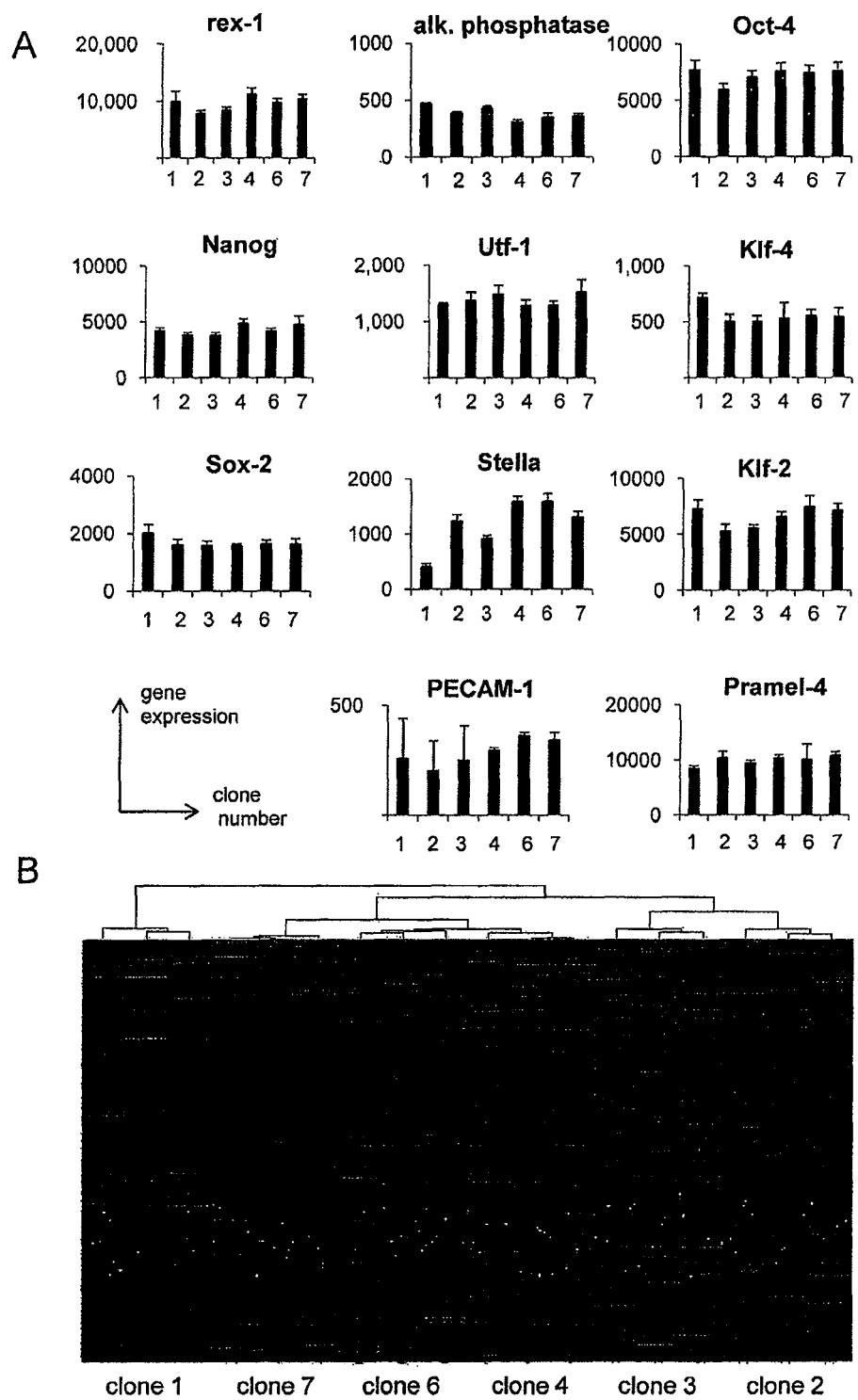
FIGS. 3A-B. mRNA expression profile in ESC sublines. A total mRNA expression profile was performed on each clonal ESC subline (FIG. 3A)—The expression of mRNA associated to pluripotency and/or early inner cell mass was established.

The observation that individual ESC in the same culture do not share the same neurogenic potential could be explained by heterogeneity between individuals or stochasticity in the decision triggering ESC neural differentiation. The hypothesis of individualities between ESC at the single cell level was investigated. Seven clonal sublines were derived from ESC by a limit dilution method. The pluripotent phenotype of each clonal subline was first investigated. Most of the tested sublines expressed markers of pluripotent cells of the early ICM including rex-1, alkaline phosphatase, Oct-4, Nanog, Klf-4, Sox-2, Klf-2, Pecam-1, and Pramel-4 (FIG. 3A). It is noteworthy that Stella expression was found in most of clones, but with a variable expression level. One clonal line (clone 5) was excluded from the study because it expressed primitive endoderm markers.

Figure 9:
FIG. 9. Presence of an unidentified derivative chromosome (der) in clones 1, 2, 6, and 7. A standard karyotype was performed for clones 1, 2, 6, and 7 at passage 16. Chromosomes were G-banded and counted, showing the additional chromosome present in the hyperploidic 41,XY preponderant population cell (*).

Clonal ESC sublines were then submitted to an analysis of their genomic structure. Standard karyotyping (G-banding) of the different clones (clones 1 to 7) was performed. The chromosome number and the presence of chromosome abnormalities were evaluated at two culture time intervals (passages 10 and 16) (Table 2). Most clones showed cell mosaicism, except clone 7 at passage 16. The normal 2n=40 frequency value in clone 3 was 36% at passage 20 and up to 60% at passage 16 (Table 2). The analysis also revealed the presence of chromosomal abnormalities. Clones 1, 2, 6, and 7 showed an identical structural rearrangement by the presence of an unidentified derivative chromosome (der) present at both passages. This rearranged chromosome was present in the hyperploidic 41,XY preponderant population cell (FIG. 9). A high resolution genomic analysis of clones was also performed by molecular karyotyping (array-CGH). This analysis revealed the presence of common partial deletion and duplication smaller than 1 Mb in all analyzed clones (Table 3). It is noteworthy that duplication on chromosome X was present in clones 1 and 2, but absent in others. The abandoned clone 5 showed a different genomic profile typified by the lack of a region in 5qE1. Taken together these results suggest that the genomic structure of the clones, with exception of clone 5, was similar and showed no major abnormalities.

TABLE 2

Standard karyotyping of ESC clones by G-banding

| Clone_passage | Number of analyzed metaphases | Karyotype | Results* |
|---|---|---|---|
| Clone 1_10 | 15 | 2 | 41, XY, +der(?)[2]/40, XY, der(?)[13] |
| Clone 1_16 | 15 | 3 | 41, XY, +der(?)[8]/40, XY, der(?)[7] |
| Clone 2_10 | 14 | 2 | 41, XY, +der(?)[10]/40, XY, der(?)[4] |
| Clone 2_16 | 16 | 2 | 41, XY, +der(?)[3]/40, XY, der(?)[13] |
| Clone 3_10 | 11 | 2 | 42, XY[7]/40, XY[4] |
| Clone 3_16 | 15 | 1 | 42, XY[2]/41, XY[3]/40, XY[9] |
| Clone 4_10 | 10 | 2 | 42, XY[4]/41, XY[1]/40, XY[2] |
| Clone 4_16 | 12 | 4 | 42, XY[5]/41, XY[4]/40, XY[2] |
| Clone 6_10 | 10 | 1 | 42, XY, +der(?)[6]/41, XY, +der(?)[4] |

TABLE 2-continued

Standard karyotyping of ESC clones by G-banding

| Clone_passage | Number of analyzed metaphases | Karyotype | Results* |
|---|---|---|---|
| Clone 6_16 | 10 | 2 | 41, XY, +der(?)[[5]/40, XY, der(?)[[4] |
| Clone 7_10 | 12 | 2 | 41, XY, +der(?)[2]/40, XY, der(?)[13] |
| Clone 7_16 | 12 | 2 | 40, XY, der(?)[9] |

TABLE 3

Genomic imbalances in clones. Regions of interest by copy number variations are reported together with their mapping position (cytogenetic band and start-end oligonucleotide positions (genome.ucsc.edu, Genome Assembly March 2006).

| Chromosome | Copy Number Variations (CNV) | Clone 1 | Clone 2 | Clone 3 | Clone 4 | Clone 6 | Clone 7 |
|---|---|---|---|---|---|---|---|
| 1 | del1qD (90,044,442-90,133,091) | + | + | + | + | + | + |
| 1 | dup1qF (141,423,792-141,591,642) | + | + | + | + | + | + |
| 2 | del2qC3 (77,680,396-77,822,003) | + | + | + | + | + | + |
| 4 | del4qB3 (61,983,292-62,007,821) | + | + | + | + | + | + |
| 4 | dup4qD2.2 (121,473,470-121,858,440) | + | + | + | + | + | + |
| 7 | del7qA3 (homozygote) (25,713,227-25,896,924) | + | + | + | + | + | + |
| 7 | del7qB3 (37,887,916-37,909,541) | + | + | + | + | + | + |
| 7 | del7qC (67,514,394-68,264,472) | + | + | + | + | + | + |
| 8 | trisomy (mosaicism) | + | + | + | + | + | + |
| 9 | dup9qA5.3 (46,630,511-46,901,471) | + | + | + | + | + | + |
| 11 | trisomy (mosaicism) | + | + | + | + | + | + |
| 11 | del11qB4 (heterozygote) 70,987,724-71,109,737 | + | + | + | + | + | + |
| 14 | dup14qA1 (3,892,581-3,983,962) | + | + | + | + | + | + |
| 17 | dup17qA1 (6,180,566-6,408,926) | + | + | + | + | + | + |
| 18 | dup18qA1 (9,813,671-10,016,566) | + | + | + | + | + | + |
| X | dupXqF4-qF5 (152,230,281-158,698,463) | + | + | − | − | − | − |

Figure 10:
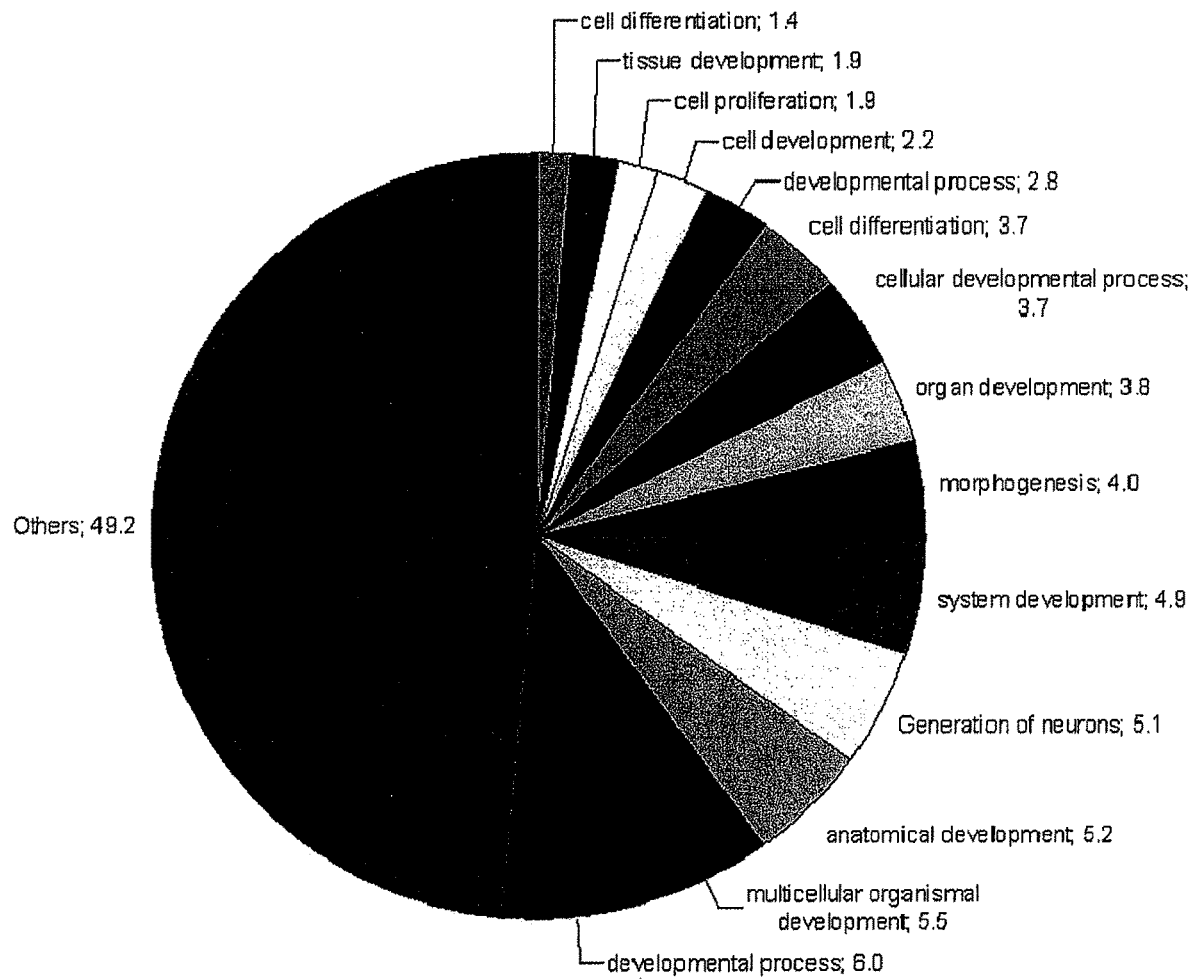
FIG. 10. Functional classification of genes which were differently expressed between ESC clones 1 and 2. Pathways were identified using MetaCore. Charts were based on 311 differentially expressed mRNA between clones 1 and 2. Percentages refer to the number of differentially expressed genes in each pathway relative to the total number of genes possessing a GO assignment.

The clonal sublines without obvious genomic abnormalities (i.e., clone 1, 2, 3, 4, 6, 7) were submitted to a total mRNA expression analysis by microarray. The expression of 6800 genes varied significantly between clonal lines (variance analysis using ANOVA statistical test). Mathematical analysis of the expression profile of these 6800 genes for each clonal ESC allowed a hierarchical clustering (FIG. 3B). The most different clonal ESC were clones 1 and 2. On the contrary, clone 2 more resembled to clone 3, as well as the couple clone 4/clone 6. FIG. 10 summarizes families of genes that were differently expressed between clones 1 and 2 (from the public database GO process (Metacore software); world wide web at genego.com). Approximately half of genes differently expressed between the two clones were classified in developmental processes, including the neuron generation. The nature of the most important changes between all clonal lines was also analyzed. In Table 4, 30 genes showing the quantitatively most important differences in expression levels between different clones are listed. The list contains several groups of genes: i) three guanylate binding proteins (Gbp 1, 2, 3); ii) three keratins (Krt 8, 18, 19); iii) two carbonic anhydrases (Car2, 4). To be noted also the couple of insulin-like growth factor 2 (Igf2) together with insulin-like growth factor binding protein 3 (Igfbp3), as well as several transcription factors.

TABLE 4

Classification of the 30 most important changes in mRNA expression between clones 1, 2, 3, 4, 6, and 7.

| | |
|---|---|
| Gbp1 | guanylate binding protein 1 (Gbp1), mRNA. |
| Acta1 | actin, alpha 1, skeletal muscle (Acta1), mRNA. |
| Gbp2 | guanylate binding protein 2 (Gbp2), mRNA. |
| Tacstd2 | tumor-associated calcium signal transducer 2 (Tacstd2), mRNA. |
| Krt8 | keratin 8 (Krt8), mRNA. |
| Igfbp3 | insulin-like growth factor binding protein 3 (Igfbp3), mRNA. |
| Krt19 | keratin 19 (Krt19), mRNA. |
| Oasl2 | 2'-5' oligoadenylate synthetase-like 2 (Oasl2), mRNA. |
| Krt18 | keratin 18 (Krt18), mRNA. |
| Sfn | stratifin (Sfn), mRNA. |
| Gbp3 | guanylate binding protein 3 (Gbp3), mRNA. |
| Car2 | carbonic anhydrase 2 (Car2), mRNA. |
| Anxa3 | annexin A3 (Anxa3), mRNA. |
| Arl4c | ADP-ribosylation factor-like 4C (Arl4c), mRNA. |

TABLE 4-continued

Classification of the 30 most important changes in mRNA expression between clones 1, 2, 3, 4, 6, and 7.

| | |
|---|---|
| Nnat | neuronatin (Nnat), transcript variant 1, mRNA. |
| Gbp3 | guanylate nucleotide binding protein 3 (Gbp3), mRNA. |
| Slc40a1 | solute carrier family 40 (iron-regulated transporter), member 1 (Slc40a1), mRNA. |
| Klk1 | kallikrein 1 (Klk1), mRNA. |
| Pitx2 | paired-like homeodomain transcription factor 2 (Pitx2), transcript variant 2, mRNA. |
| Flnc | filamin C, gamma (Flnc), mRNA. |
| Bhlhb2 | basic helix-loop-helix domain containing, class B2 (Bhlhb2), mRNA. |
| Ampd3 | adenosine monophosphate deaminase 3 (Ampd3), mRNA. |
| Dok2 | docking protein 2 (Dok2), mRNA. |
| Bmp1 | bone morphogenetic protein 1 (Bmp1), mRNA. |
| Ddit3 | DNA-damage inducible transcript 3 (Ddit3), mRNA. |
| Efna5 | ephrin A5 (Efna5), transcript variant 2, mRNA. |
| Ddit3 | DNA-damage inducible transcript 3 (Ddit3), mRNA. |
| Car4 | carbonic anhydrase 4 (Car4), mRNA. |
| Igf2 | insulin-like growth factor 2 (Igf2), mRNA. |
| Sp5 | trans-acting transcription factor 5 (Sp5), mRNA. |

In Table 4, the expression level of all transcripts was compared between clones. A value corresponding to the standard deviation was normalized with the average of transcript expression between clones. All transcripts were classified according the ratio between standard deviation and expression level. The table provides a list of the 30 first genes associated with the higher ratio.

Figure 4:
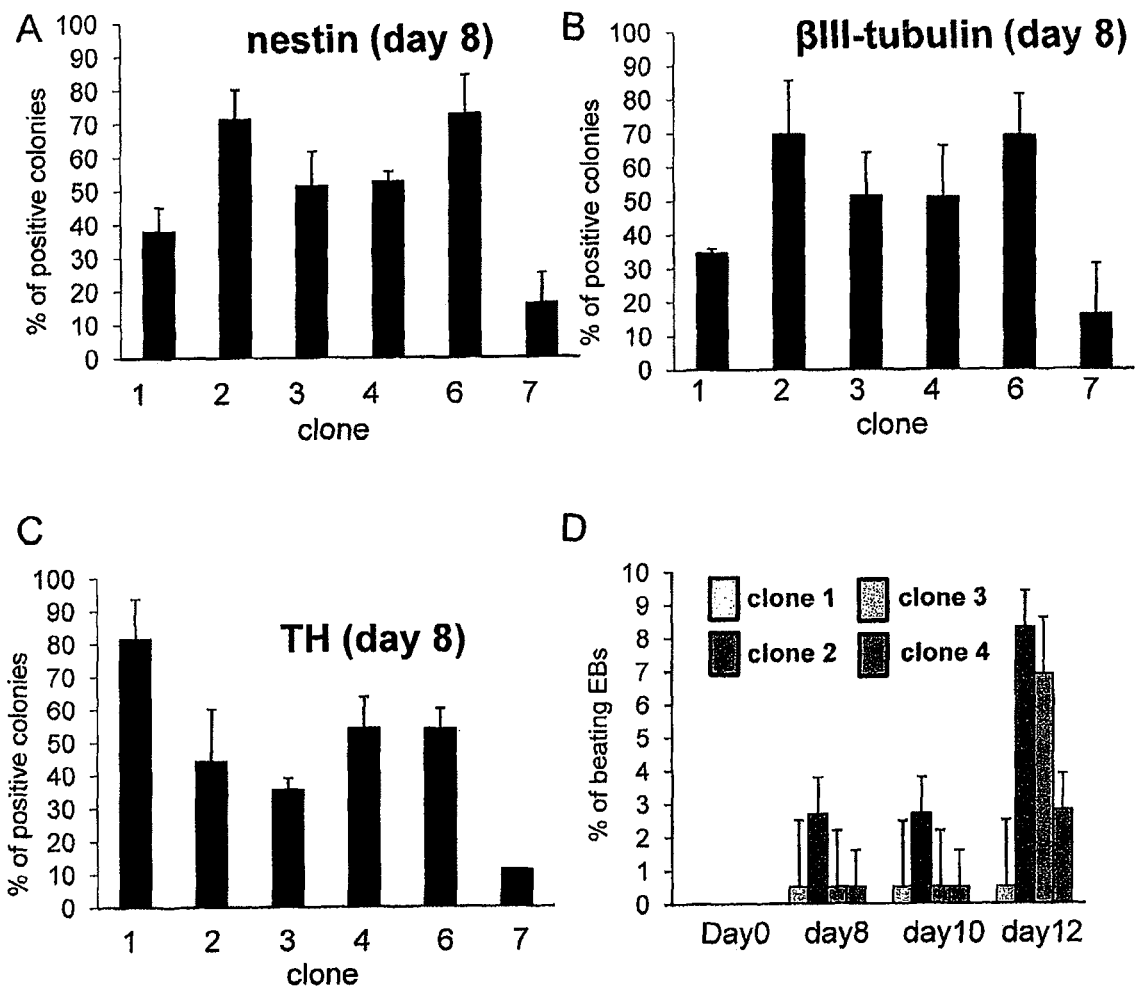
FIGS. 4A-D. Clonal ESCs do not share the neurogenic and cardiogenic potential.

The inventors hypothesized that these differences in mRNA expression levels might confer a propensity for specific differentiation pathways to the different clones. To investigate variability at the functional level, clonal ESC were submitted to neural differentiation by co-culture with PA6 stromal cells. All lines induced both neural and non-neural colonies. However, the ratio between neural and non-neural colonies differed between clones. Clones 2 and 6 generated a significantly higher percentage of colonies including neuroepithelial cells (nestin+) than clone 7 (FIG. 4A). This increased capacity of clones 2 and 6 was confirmed by neuronal βIII-tubulin staining (FIG. 4B). After one week differentiation and in accordance with these observations, clone 7 had a lower capacity to generate colonies with TH dopaminergic neurons (FIG. 4C). It is noteworthy that clone 1 induced a higher number of TH-positive colonies than other clones. Clones varied also in their cardiogenic potential. Clones 2 and 3 were significantly more efficient than clone 4 to produce beating cardiomyocytes. In contrast, clone 1 was not efficient to generate cardiac cells (FIG. 4D).

Figure 5:
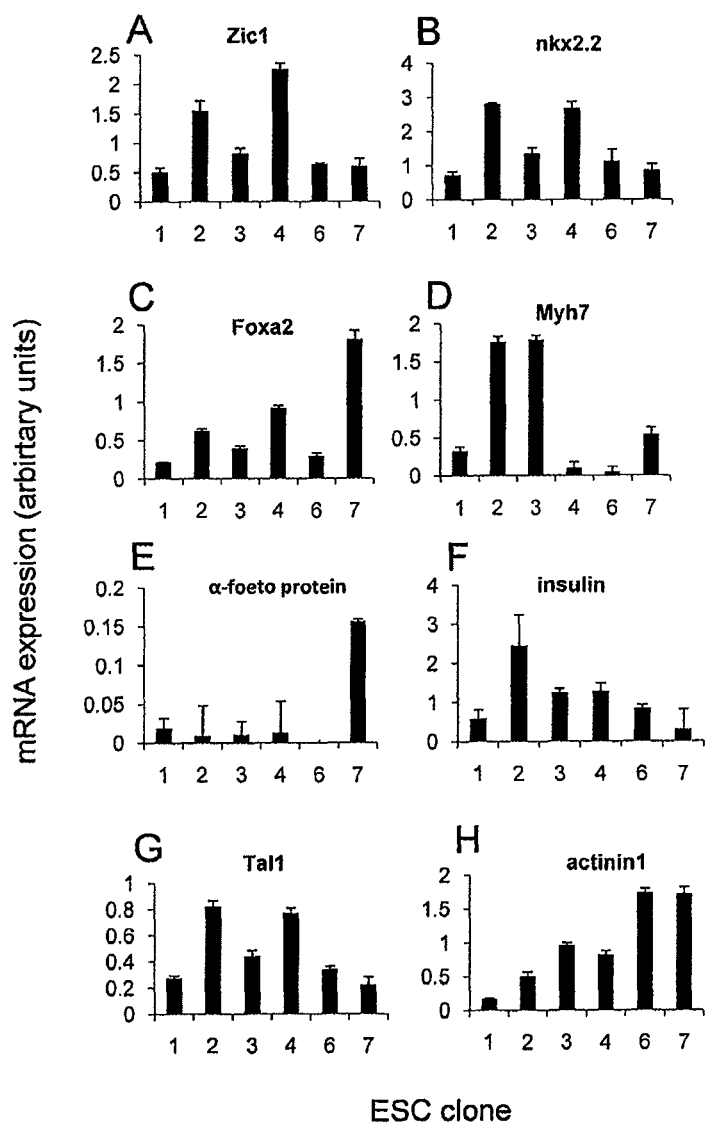
FIGS. 5A-H. Clonal ESC do not share the same differentiation potential. ESC clones were differentiated in vitro towards embryoid bodies and assessed by quantitative PCR for the expression of genes specific for different histological types and germ layers.

Under appropriate conditions, all sublines had the capacity to generate floating embryoid bodies. Expression of genes which are linked to different germ layers/cell types was then quantified in embryoid bodies after two weeks. The expression of all of the analyzed genes differed between clones (FIGS. 5A-H). A heterogeneous expression of the ectodermal Zic1 (FIG. 5A) and neuroectodermal nkx2.2 (FIG. 5B) was observed, suggesting variability in the neurogenic potential of ESC clones. Heterogenity was also observed using the endodermal gene Foxa2 (FIG. 5C). Clones 2 and 3 induced higher levels of the cardiac marker Myh7 (FIG. 5D), whereas the hepatic α-foeto protein was more generated in clone 7 (FIG. 5E). Variability was also observed in the capacity of clones to generate the pancreatic insulin (FIG. 5F), as well as the mesodermal Tal1 (FIG. 5G) and muscle cells actinin1 (FIG. 5H).

Taken together, these data show that clonal lines do not share the same differentiation potential and confirm that individual pluripotent ESCs in the same culture are functionally heterogeneous.

Figure 6:
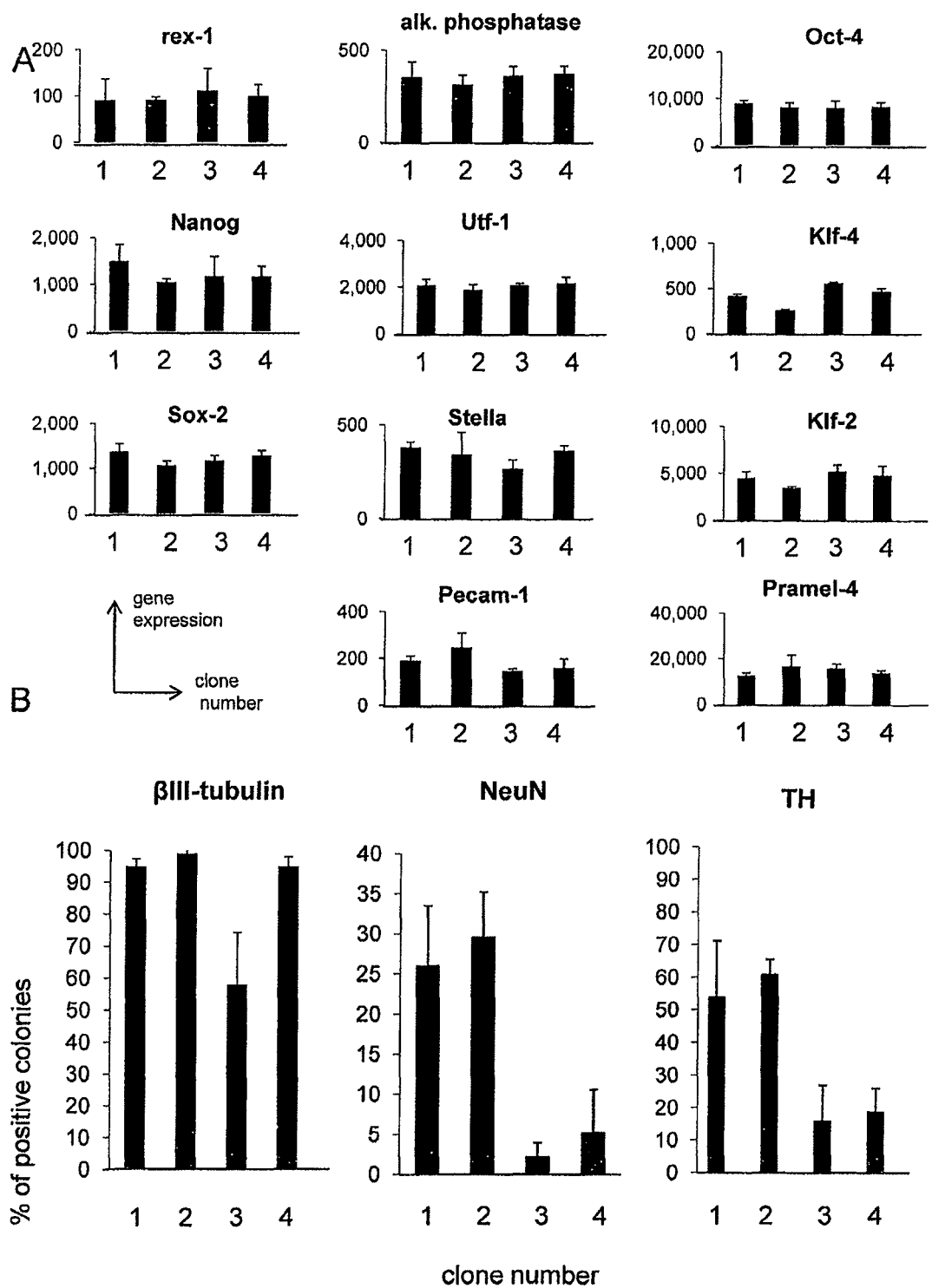
FIGS. 6A-B. Clonal sublines from D3 ESC confirms cellular diversity. A total mRNA expression profile was performed on each clonal D3 subline (FIG. 6A)—The expression of mRNA associated to pluripotency and/or early inner cell mass was established.

This concept of clonal heterogeneity was also tested in another ESC line (D3). Sublines were generated from D3 by the limit dilution method and each clone was submitted to genomic analysis and total gene expression profile. As observed for the CGR8 line, there were no major genomic abnormalities among sublines. Gene expression array was performed and all of the pluripotency markers corresponding to the early ICM were detected in the clones (FIG. 6A). D3 sublines differed significantly in their capacity to generate colonies including βIII-tubulin+ neurons (FIG. 6B), NeuN+ mature stage neurons (FIG. 6C) and TH+ dopaminergic neurons (FIG. 6D), confirming cellular individualities in ESC.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,352,883
U.S. Pat. No. 4,366,241
U.S. Pat. No. 4,683,195
U.S. Pat. No. 4,683,202
U.S. Pat. No. 4,800,159
U.S. Pat. No. 5,843,780
U.S. Pat. No. 6,200,806
U.S. Pat. No. 6,325,114
U.S. Pat. No. 6,833,269
U.S. Pat. No. 7,029,913
U.S. Pat. No. 7,473,555
U.S. Patent Publn. 2005/0042750
U.S. Patent Publn. 2006/0084168
U.S. Patent Publn. 2007/0010012
U.S. Patent Publn. 2008/0031857
U.S. Patent Publn. 2008/0187494
U.S. Patent Publn. 2010/0086525
U.S. Patent Publn. 2010/0129351
U.S. Patent Publn. 2010/0143313
U.S. Patent Publn. 2010/0086999
A Practical Approach, Robertson (Ed.), IRL Press Ltd., 1987.
Amit et al., Dev. Bio., 227:271-278, 2000.
Animal Cell Culture, Freshney (Ed.), 1987
Byrne et al., Nature, 450(7169):497-502, 2007.
Chalfie et al., Science, 263(5148):802-805, 1994.
Current Protocols in Molecular Biology and Short Protocols in Molecular Biology, 3rd Edition (Ausubel et al., Eds.), 1987 & 1995.
Davies et al., Biochem. J., 351(Pt 1):95-105, 2000.
Eiraku et al., Cell Stem Cell, 3(5):519-32, 2008.
Embryonic Stem Cell Differentiation In Vitro, 1993
Gene Transfer Vectors for Mammalian Cells, Miller & Calos (Eds.), 1987
Griffiths, In: Animal Cell Biotechnology, 3:179-220, Spier and Griffiths (Eds.), Academic Press, London., 1986.

Guide to Techniques in Mouse Development, Wasserman et al. (Eds.), Academic Press, 1993.
Ikenoya et al., *J. Neurochem.*, 81(1):9-16, 2002.
Innis et al., *Proc. Natl. Acad. Sci. USA*, 85(24):9436-9440, 1988.
Itskovitz-Eldor et al., *Mol. Med.*, 6:88B95, 2000.
Li et al., *Mol. Biol. Cell.*, 17:3978-3988, 2006.
Ludwig et al., *Nat. Biotechnol.*, 24(2):185-187, 2006b.
Ludwig et al., *Nat. Methods*, 3(8):637-46, 2006a.
Lyons, *J. Immunol. Methods*, 243(1-2):147-54, 2000.
Maekawa et al., *Science*, 285(5429):895-8, 1999.
Martin, *Proc. Natl. Acad. Sci. USA*, 78:7634B7638; 1982.
PCT Appln. WO 01/51616
PCT Appln. WO 2010/049752A1
PCT Appln. WO 94/17178
*Properties and uses of Embryonic Stem Cells: Prospects for Application to Human Biology and Gene Therapy*, 1998
Reubinoff et al., *Nat. Biotechnol.*, 18:399B404, 2000.
Rietze and Reynolds, *Methods Enzymol.*, 419:3-23, 2006.
Roach et al., *Eur. Urol.*, 23:82B87, 1993.
Sancho-Bru et al., *Gut.* 58(4):594-603, 2009.
Sasaki et al., *Pharmacol. Ther.*, 93(2-3):225-32, 2002.
Schmandt et al., *Stem Cells Dev.*, 14:55-64, 2005.
Shintani, *J. Neurosci. Res.*, 86(13):2829-38, 2008.
Si-Tayeb et al., *Hepatology*, 51(1):297-305, 2010.
Smith, In: *Origins and Properties of Mouse Embryonic Stem Cells*, Annu. Rev. Cell. Dev. Biol., 2000.
Suter et al., *J. Cell Mol. Med.*, 2009 (Epub ahead of print)
Svendsen et al., *Brain Pathol.*, 9:499-513, 1999.
Takahashi and Yamanaka, *Cell*, 126:663-676, 2006.
Takahashi et al., *Cell*, 126(4):663-76, 2007.
Takahashi et al., *Cell*, 131:861-872, 2007.
Thomson and Marshall, *Curr. Top. Dev. Biol.*, 38:133-165, 1998.
Thomson and Odorico, *J. Trends. Biotechnol.*, 18:53B57, 2000.
Thomson et al. *Proc. Natl. Acad. Scie. USA*, 92:7844-7848, 1995.
Thomson et al., *Science*, 282:1145, 1998.
van Wezel, *Nature*, 216(5110):64-5, 1967.
Xu et al., *Nat. Biotechnol.*, 19:971-974, 2001.
Ying et al., *Cell*, 115:281-292, 2003.
Yu and Thompson, *Genes Dev.* 22(15):1987-97, 2008.
Yu et al., *Science*, 318:1917-1920, 2007.
Zaret et al., *Science*, 322(5907):1490-1494, 2008.

What is claimed is:

1. A method for selecting a clonal population of undifferentiated pluripotent stem cells, the method comprising the steps of:
   a) obtaining a first clonal population of undifferentiated pluripotent stem cells that has been expanded in vitro and maintained in an undifferentiated state;
   b) individualizing and expanding cells of the first clonal population to provide at least two individual, expanded second clonal populations of undifferentiated cells;
   c) differentiating cells of the at least two individual second clonal population into cells of a differentiated cell type; and
   d) selecting and expanding individualized, undifferentiated cells of the at least two individual second clonal populations that differentiate into the selected differentiated cell type.

2. The method of claim 1, wherein the pluripotent cells are human embryonic stem cells.

3. The method of claim 1, wherein said pluripotent cells are induced pluripotent cells (iPSC).

4. The method of claim 1, further comprising providing the selected individual second clonal population of cells.

5. The method of claim 1, further comprising preparing the selected individual second clonal population of cells for storage or shipment.

6. The method of claim 5, wherein preparing the cells for storage or shipment comprises freezing the cells.

7. The method of claim 1, wherein step c) comprises exposing the expanded second clonal populations of cells to a test compound and measuring a cellular parameter associated with toxicity in the expanded cells.

8. The method of claim 1, wherein the first clonal population of cells are human cells.

9. The method of claim 1, wherein step c) comprises differentiating at least three individualized, undifferentiated cells of at least three individual second clonal populations into a differentiated cell type determining the ability of at least 3 individual second clonal populations to differentiate into a population of cells of the selected cell type.

10. The method of claim 9, wherein step c) comprises differentiating at least three individualized, undifferentiated cells of at least five individual second clonal populations into a differentiated cell type determining the ability of at least 3 individual second clonal populations to differentiate into a population of cells of the selected cell type.

11. The method of claim 1, wherein step c) comprises differentiating at least eight individualized, undifferentiated cells of at least eight individual second clonal populations into a differentiated cell type determining the ability of at least 3 individual second clonal populations to differentiate into a population of cells of the selected cell type.

12. The method of claim 1, wherein step c) comprises differentiating at least ten individualized, undifferentiated cells of at least ten individual second clonal populations into a differentiated cell type determining the ability of at least 3 individual second clonal populations to differentiate into a population of cells of the selected cell type.

13. The method of claim 1, wherein the selected differentiated cell type is neural cells, hepatocytes or cardiomyocytes.

14. The method of claim 13, wherein the selected differentiated cell type is neural cells.

15. The method of claim 13, wherein the selected differentiated cell type is hepatocytes.

16. The method of claim 13, wherein the differentiated cell type is cardiomyocytes.

17. A method for selecting a clonal population of pluripotent stem cells, comprising the steps of:
   a) obtaining a first clonal population of undifferentiated pluripotent stem cells that has been expanded in vitro and maintained in an undifferentiated state;
   b) individualizing and expanding the cells of the first clonal population to provide at least two individual expanded second clonal populations of undifferentiated cells;
   c) differentiating at least two individualized cells of the second clonal populations cells for their ability to differentiate into a population of neural cells, hepatocytes or cardiomyocytes as compared to other second clonal populations; and
   d) selecting and expanding individualized, undifferentiated cells of the second clonal population tested and determined to have a greater ability to differentiate into neural cells, hepatocytes or cardiomyocytes.

18. The method of claim 17, wherein the second clonal population is differentiated into neural cells.

19. The method of claim 17, wherein the second clonal population is differentiated into hepatocytes.

20. The method of claim 17, wherein the second clonal population is differentiated into cardiomyocytes.

21. The method of claim 17, wherein said pluripotent cells are induced pluripotent cells (iPSC).

22. The method of claim 17, further comprising preparing the selected individual second clonal population of cells for storage or shipment.

23. The method of claim 22, wherein preparing the cells for storage or shipment comprises freezing the cells.

24. The method of claim 17, wherein step c) comprises exposing the expanded second clonal populations of cells to a test compound and measuring a cellular parameter associated with toxicity in the expanded cells.

25. The method of claim 1, wherein the first clonal population of cells are human cells.

\* \* \* \* \*

UNITED STATES PATENT AND TRADEMARK OFFICE
CERTIFICATE OF CORRECTION

| | | |
|---|---|---|
| PATENT NO. | : 10,947,499 B2 | Page 1 of 1 |
| APPLICATION NO. | : 12/958183 | |
| DATED | : March 16, 2021 | |
| INVENTOR(S) | : Preynat-Seauve et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2216 days.

Signed and Sealed this
Seventh Day of February, 2023

*Katherine Kelly Vidal*

Katherine Kelly Vidal
*Director of the United States Patent and Trademark Office*